(12) United States Patent
Pandey et al.

(10) Patent No.: US 9,242,926 B2
(45) Date of Patent: *Jan. 26, 2016

(54) PROCESSES FOR THE PREPARATION OF LACOSAMIDE AND INTERMEDIATES THEREOF

(71) Applicant: CADILA HEALTHCARE LIMITED, Ahmedabad, Gujarat (IN)

(72) Inventors: Bipin Pandey, Ahmedabad (IN); Kalpesh Shah, Ahmedabad (IN)

(73) Assignee: CADILA HEALTHCARE LIMITED, Ahmedabad (IN)

(*) Notice: Subject to any disclaimer, the term of this patent is extended or adjusted under 35 U.S.C. 154(b) by 0 days.

This patent is subject to a terminal disclaimer.

(21) Appl. No.: 14/302,749

(22) Filed: Jun. 12, 2014

(65) Prior Publication Data

US 2014/0296572 A1    Oct. 2, 2014

Related U.S. Application Data

(62) Division of application No. 13/394,879, filed as application No. PCT/IN2010/000642 on Sep. 23, 2010, now Pat. No. 8,853,439.

(30) Foreign Application Priority Data

Sep. 25, 2009 (IN) .......................... 2232/MUM/2009
Jun. 4, 2010 (IN) .......................... 1719/MUM/2010

(51) Int. Cl.
| | |
|---|---|
| C07C 271/02 | (2006.01) |
| C07C 231/14 | (2006.01) |
| C07C 231/24 | (2006.01) |
| C07C 271/22 | (2006.01) |
| C07C 237/22 | (2006.01) |
| C07C 231/12 | (2006.01) |

(52) U.S. Cl.
CPC ............. *C07C 231/12* (2013.01); *C07C 231/24* (2013.01); *C07C 237/22* (2013.01); *C07C 271/22* (2013.01)

(58) Field of Classification Search
CPC ........................... C07C 237/22; C07C 27/221
USPC ........................................... 560/24, 163, 141
See application file for complete search history.

(56) References Cited

U.S. PATENT DOCUMENTS

| 2005/0075281 A1 | 4/2005 | Von Nussbaum |
| 2009/0143472 A1 | 6/2009 | Madhra |

FOREIGN PATENT DOCUMENTS

| WO | 2004099239 A1 | 11/2004 |
| WO | 2006037574 A1 | 4/2006 |
| WO | 2006102283 A2 | 9/2006 |
| WO | 2009146325 A1 | 12/2009 |

OTHER PUBLICATIONS

Choi et al. Journal of Medicinal Chemistry, 1996, 39(9), p. 1907-1916.*
Currie, G. et al: "Chirally templated boronic acid Mannich reaction in the synthesis o optically active a-amino acids", Journal of the Chemistry Society, Perkins Transactions 1, No. 17, 2000, pp. 2982-2990, XP008132917.
Choi, D. et al: "Synthesis and anticonvulsant activities of N-benzyl-2-acetamidoproprionamide derivatives", Journal of Medicinal Chemistry, Washington, US, vol. 39, 1996, pp. 1907-1916, XP002584636.
Di Giovanni, Maria C. et al: "A Stereoselective Synthesis of 3(R)-Hydroxy-2(S)-ornithine", Tetrahedron, vol. 49, No. 48, 1993, pp. 11321-11328, XP002621426.
Chatterjee, S. et al: "D-Amino Acid Containing High-Affinity Inhibitors of Recombinant Human Calpain I", Journal of Medicinal Chemistry, American Chemical Society, Washington, US, vol. 41, No. 15, Jul. 16, 1998, pp. 2663-266, XP002155160.
Crane, Christine. M. et al: "Synthesis and Evaluation of Vancomycin Aglycon Analogues That Bear Modifications in the N-Terminal D-Leucyl Amino Acid", Jjournal of Medicinal Chemistry, vol. 52, No. 5, 2009, pp. 1471-1476, XP002621425.
Lorenz, K B et al: "Solution-Phase Synthesis of Nucleobase-Substituted Analogues of Triostin A", Journal of Organic Chemistry, American Chemical Society, Easton.; US, vol. 69, No. 11, May 28, 2004, pp. 3917-3927, XP002319426.
International Search Report for PCT/IN2010/000642; Search Authority: European Patent Office; Search Completed: Mar. 16, 2011; Authorized Officer: Fitz, Wolfgang.

* cited by examiner

*Primary Examiner* — Yong Chu
(74) *Attorney, Agent, or Firm* — IpHorgan Ltd.

(57) ABSTRACT

The invention relates to improved processes for the preparation of lacosamide. The invention also relates to a novel intermediate useful in the preparation of lacosamide. The invention also relates to process for the purification of lacosamide.

5 Claims, No Drawings

PROCESSES FOR THE PREPARATION OF LACOSAMIDE AND INTERMEDIATES THEREOF

CROSS REFERENCE TO RELATED APPLICATIONS

This application is divisional application of U.S. patent application Ser. No. 13/394,879, filed May 2, 2012, now U.S. Pat. No. 8,853,439, which is a national phase application under 35 U.S.C. 371 of international patent application PCT/IN2010/000642, having an international filing date of Sep. 23, 2010, and claiming priority to Indian patent application no. 1719/MUM/2010, filed Jun. 4, 2010 and Indian patent application no. 2232/MUM/2009, filed Sep. 25, 2009.

FIELD OF THE INVENTION

The invention relates to an improved process for the preparation of lacosamide. The invention further relates to the preparation of novel intermediates and their use in the preparation of lacosamide.

BACKGROUND OF THE INVENTION

Lacosamide is marketed under the trade name Vimpat®. Lacosamide is chemically 2(R)-acetamido-N-benzyl-3-methoxypropionamide and has the structural Formula (I).

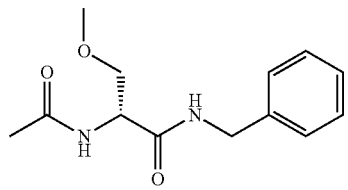

(I)

U.S. Pat. No. 5,654,301 discloses certain compounds which are amino acid derivatives and includes lacosamide. Various synthetic schemes for the preparation of these derivatives are disclosed.

Lacosamide and its methods of preparation are disclosed in U.S. Reissue Pat. No. RE 38,551. The patent provides three general methods for the preparation of lacosamide. The first two methods do not involve the protection of active groups in intermediate compounds (such as amino, hydroxy and carboxylic acid groups). The other method disclosed in this patent involves protection of an amino group present in D-serine with carbobenzoxy chloride (Cbz-Cl), subsequent O-methylation at the hydroxy group followed by amidation at carboxylic (—COOH) acid with benzylamine and finally removal of the 'Cbz' group followed by acetylation, to produce lacosamide.

An alternative method for the preparation of lacosamide is disclosed in International (PCT) Publication No. WO 2006/037574 that involves O-methylation of N-Boc-protected-D-serine ("Boc" refers to t-butoxycarbonyl) directly in one step by avoiding simultaneous formation of the methyl ester moiety.

US 20090143472 disclose certain intermediates and methods of preparation of lacosamide using the intermediates. The process of preparation of lacosamide involves O-methylation of the intermediate, benzyl amine amidation, detritylation and finally acetylation to yield lacosamide. Another method disclosed involves first benzyl amine amidation of the intermediate, and then O-methylation, subsequently followed by detritylation and finally acetylation.

WO2010052011 discloses the resolution of 2-acetamido-N-benzyl-3-methoxypropionamide using chiral chromatography.

In view of the preparation methods available for lacosamide, there is a need for simple and cost effective processes for the preparation of lacosamide that provides improved efficiency per reaction volume in terms of yield, and purity, both chemical and chiral.

SUMMARY OF THE INVENTION

In one general aspect, there is provided a novel process for the preparation of lacosamide. The process includes:

a) reacting a compound of Formula II,

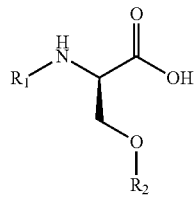

Formula II with benzyl amine to give a compound of Formula III,

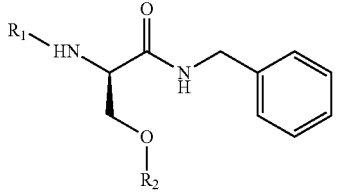

Formula III wherein $R_1$ is a suitable amine protecting group selected from Boc, Fmoc, Cbz, Tos and the like; and $R_2$ is suitable hydroxyl protecting group selected from benzyl, tertiary butyl, benzoyl, and the like;

b) deprotecting the amino protecting group $R_1$ of Formula III to obtain a compound of Formula IV,

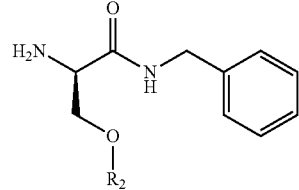

Formula IV wherein $R_2$ is a suitable hydroxyl protecting group selected from benzyl, tertiary butyl, and benzoyl;

c) acetylating the compound of Formula IV to obtain a compound of Formula V,

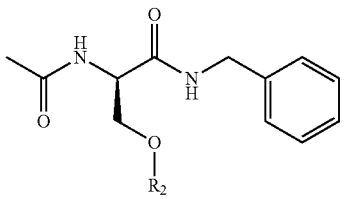

Formula V wherein $R_2$ is a suitable hydroxyl protecting group selected from benzyl, tertiary butyl, and benzoyl;

d) deprotecting the hydroxyl protecting group $R_2$ of Formula V to obtain a compound of Formula VI; and

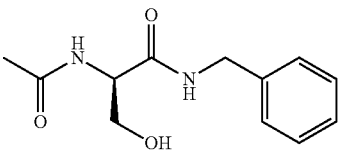

Formula VI e) O-methylating the alcoholic group of compound of Formula VI to obtain lacosamide of Formula I.

Embodiments of the process may include one or more of the following features. For example, the reaction of the compound of Formula II with benzyl amine may be carried out in the presence of a suitable base, and suitable carboxylic acid activator in the presence of one or more suitable solvents. The deprotection of $R_1$ group of Formula III may be carried out in the presence of a suitable deprotecting agent and one or more suitable solvents. The suitable deprotecting agent may be selected from those disclosed in Text book—Title: *Protective Groups in Organic Synthesis, 3rd Edition*, John Wiley and Sons, By—T. W. Grene and Peter G. M. Wuts). The acetylation of the compound of Formula IV may be carried out in the presence of a suitable acetylating agent and one or more suitable solvents. Finally, the deprotection of $R_2$ group may be carried out in the presence of suitable deprotecting agents such as one or more suitable bases in one or more suitable solvents based on particular protecting group, and O-methylation of the alcoholic group of compound of Formula VI may be carried out in the presence of a suitable methylating agent in the presence of a suitable organometallic compound, optionally in the presence of a suitable phase transfer catalyst.

In another general aspect, there is provided a compound of Formula (II),

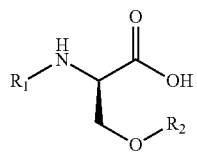

wherein $R_1$ is a suitable amino protecting group selected from Boc, Fmoc, Cbz, Tos and the like; and $R_2$ is a suitable hydroxyl protecting group selected from benzyl, tertiary butyl, benzoyl, and the like.

In another aspect there is provided a process for the purification of lacosamide. The process includes obtaining a solution of lacosamide in one or more suitable solvents and recovering pure lacosamide by removal of the solvents.

In particular, the process includes obtaining a solution of lacosamide in one or more solvents; adding an anti-solvent to the solution; and isolating the pure lacosamide by removing the solvents.

Removing the solvent may include, for example, one or more of distillation, distillation under vacuum, evaporation, filtration, filtration under vacuum, decantation and centrifugation.

Embodiments of the process may include one or more of the following features. For example, the solution of lacosamide may be obtained by heating or stirring, or a combination of both.

The product so obtained may be further or additionally purified to obtain desired purity levels.

The process may include further forming the product so obtained into a finished dosage form.

The process may produce the pure lacosamide having a purity of more than 99% by HPLC.

The details of one or more embodiments of the inventions are set forth in the description below. Other features, objects and advantages of the inventions will be apparent from the description.

DETAILED DESCRIPTION OF THE INVENTION

As used herein, the term "reflux temperature" refers to the boiling point of the solvent.

As used herein, the term "THF" refers to tetrahydrofuran, the term "DCM" refers to dichloromethane, the term "DMF" refers to dimethylformamide, the term "IPA" refers to isopropyl alcohol, the term "DIPE" refers to diisopropyl ether, the term "MIBK" refers to methyl isobutyl ketone, the term "PTC" refers to phase transfer catalyst, the term "Boc" refers to tert-Butyloxycarbonyl group, the term "Fmoc" refers to 9-fluorenylmethoxycarbonyl group, the term "Cbz or Z" refers to carbobenzyloxy group, the term "Tos" refers to tosyl group, "TFA" refers to trifluoroaceticacid, HCl refers to hydrochloric acid, "$H_2$" refers to hydrogen, "Pd/C" refers to palladium-charcoal, "HBr" refers to hydrobromic acid, "HF" refers to hydrofluoric acid "MTBE" refers to methylter terybutyl ether, "HPLC" refers to High Performance Liquid Chromatography, "t-butyl" refers to tertiary-butyl, "LDA" refers to lithium diisopropylamide, "LHMDS" refers to lithium hexamethyldisilazide, NaOH refers to sodium hydroxide, "DMSO" refers to dimethyl sulfoxide, "MS" refers to mass, "IR" refers to infrared, "KBr" refers to potassium bromide, "g" refers to gram, "mL" refers to milliliter, "MeOH" refers to methanol, "aq" refers to aqueous.

The inventors have developed a process for the preparation of lacosamide using novel intermediate of Formula (II). The process includes:

a) reacting a compound of Formula II

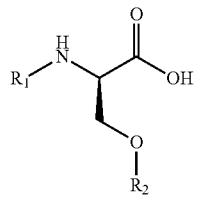

Formula II with benzyl amine to give a compound of Formula III,

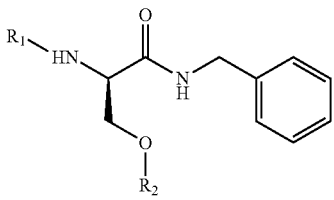

Formula III wherein $R_1$ is a suitable amino protecting group selected from Boc, Fmoc, Cbz, Tos, and the like; and $R_2$ is a hydroxyl protecting group selected from benzyl, tertiary butyl, benzoyl, and the like;

b) deprotecting amino protecting group $R_1$ of Formula III to obtain a compound of Formula IV,

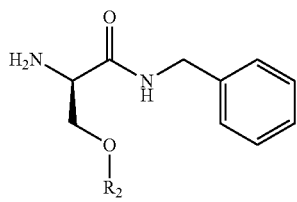

Formula IV wherein $R_2$ is a hydroxyl protecting group selected from benzyl, tertiary butyl, benzoyl, and the like;

c) acetylating the compound of Formula IV to obtain compound of Formula V,

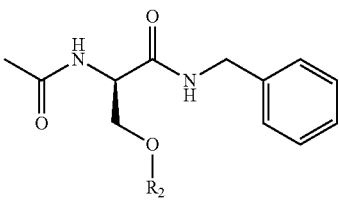

Formula V wherein $R_2$ is a hydroxyl protecting group selected from benzyl, tertiary butyl, benzoyl, and the like;

d) deprotecting the hydroxyl protecting group $R_2$ of Formula V to obtain a compound of Formula VI; and

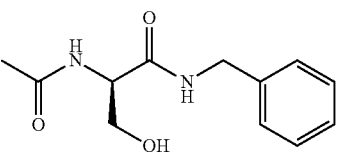

Formula VI e) O-methylating the alcoholic group of the compound of Formula VI to obtain the lacosamide of Formula I.

In general, the reaction of the compound of Formula (II) with benzyl amine may be carried out in the presence of a suitable base and suitable carboxylic acid activator in the presence of suitable solvent. Suitable bases may include one or more of morpholine, N-methyl morpholine, triethylamine, diethylamine, isopropyl amine, and the like. In particular, N-methyl morpholine may be used.

Suitable solvents which can be used at step (a) may include one or more of dichloromethane, trichloromethane, tetrachloromethane, ethyl acetate, toluene, tetrahydrofuran, and the like. In particular, the reaction may be carried out in tetrahydrofuran.

Suitable carboxylic acid activators may include optionally substituted alkyl or aryl chloroformates such as methyl chloroforamte, isobutyl chloroformate, phenyl chloroformate, nitro-phenyl chloroformate and the like; suitable azoles such as 1-hydroxybenotriazole, and the like or suitable imides such as 1,3-dicyclohexylcarbodimide, 1-ethyl-3-(3-dimethlaminopropyl)carbodimide, and the like.

The deprotection of the $R_1$ group of compound of Formula (III) may be carried out by using a suitable deprotecting agent which can be used at step (b) and may be selected from those disclosed in Text book—Title: *Protective Groups in Organic Synthesis, 3$^{rd}$ Edition*, John Wiley and Sons, By—T. W. Grene and Peter G. M. Wuts).

In one embodiment, the deprotection of the $R_1$ group of compound of Formula (III) may be carried out in the presence of a suitable acid in a suitable solvent, when $R_1$ is Boc. Suitable acid may include one or more of TFA, aq. HCl, and the like. In particular, TFA may be used.

Examples of the solvents which may be used for step-(b) (when $R_1$ is Boc) include one or more of chlorinated hydrocarbons such as chloroform, DCM, 1,2 dichloroethane, and the like. In particular, DCM may be used.

In another embodiment, the deprotection of the $R_1$ group of compound of Formula (III), may be carried out in the presence of a suitable amine base in the presence of a suitable solvent under mild conditions, when $R_1$ is Fmoc. Suitable amine base may include one or more of 20% piperidine, 50% morpholine, and the like. In particular, 20% piperidine may be used.

Examples of the solvent which may be used for step-(b) (when $R_1$ is Fmoc) include one or more of polar solvents such as tetrahydrofuran, ethyl acetate, dimethylsulfoxide, acetonitrile and the like. In particular, DMF may be used.

The deprotection of the $R_1$ group of compound of Formula (III) may be carried out in the presence of $H_2$ atmosphere and % of Pd/C 5 to 10% in a suitable solvent, when $R_1$ is Cbz.

Examples of the solvents which may be used for step-(b) (when $R_1$ is Cbz) include one or more of $C_1$ to $C_6$ alcohols such as methanol, ethanol, propanol, isopropanol, butanol, isobutanol, pentanol, isopentanol, hexanol and the like. In particular, methanol may be used.

The deprotection of the $R_1$ group of compound of Formula (III) may be carried out in the presence of one or more of HBr in acetic acid, HF/Pyridine, or anisole, when $R_1$ is Tos. In particular, HBr in acetic acid may be used.

The acetylation of the compound of Formula (IV) may be carried out by using suitable acetylating agents.

Suitable acetylating agents may include one or more of acetic anhydride, acetyl chloride, acetic acid, and the like and derivatives thereof, or mixtures thereof. Suitable bases which may be used at step (c) may include pyridine, dimethylamino pyridine, and the like.

The acetylation may be performed in suitable solvents at temperature in the range from about 20° C. to about 70° C., for example from about 50° C. to about 70° C. In particular, it may be carried out at a temperature of about 60° C. Examples of the solvents which may be used for step-(c) include dichloromethane, toluene, ethyl acetate, or mixtures thereof.

The deprotection of the $R_2$ group of compound of Formula (III) may be carried out by using suitable deprotecting agent which can be used at step (d) and may be selected from those disclosed in Text book—Title: *Protective Groups in Organic Synthesis*, 3$^{rd}$ Edition, John Wiley and Sons, By—T. W. Grene and Peter G. M. Wuts).

In one embodiment, the deprotection of the $R_2$ group of compound of Formula (III) may be carried out in the presence of $H_2$ atmosphere and % of Pd/C 5 to 10% in a suitable solvent, when $R_2$ is benzyl.

Examples of the solvents which may be used for step-(d) (when $R_2$ is benzyl) includes one or more of $C_1$ to $C_6$ alcohols such as methanol, ethanol, propanol, isopropanol, butanol, isobutanol, pentanol, isopentanol, hexanol and the like. In particular, methanol may be used.

The deprotection of the $R_2$ group of compound of Formula (III) may be carried out in the presence of a suitable acid in a suitable solvent, when $R_2$ is t-butyl. Suitable acids may include one or more of TFA, aq. HCl and the like. In particular, TFA may be used.

Examples of the solvents which may be used for step-(d) (when $R_2$ is t-butyl) include one or more of halogenated hydrocarbon such as chloroform, DCM, 1,2 dichloroethane and the like. In particular, DCM may be used.

In general, the O-methylation of the alcoholic group of compound of Formula VI can be carried out using phase transfer catalysis (PTC).

The process includes adding a suitable methylation reagent to a mixture of two phases in the presence of a phase transfer catalyst. The methylating agent may include one or more of dimethylsulfate, methyl iodide or trimethyl phosphate. The first phase may be an aqueous phase and may include an alkaline aqueous solution, such as aqueous sodium hydroxide, aqueous lithium hydroxide, or aqueous potassium hydroxide. The second phase may be an organic phase and may include toluene, hexane, methylene chloride or methyl t-butyl ether.

Suitable phase transfer catalyst which can be used at step (e) may include one or more of tetraethylammonium p-toluenesulfonate, tetrapropylammonium trifluoromethanesulfonate, tetraphenylphosphonium hexafluroantimonate, ethylpyridinium bromide, triphenylmethyl triphenylphosphonium chloride, benzyltriethylammonium chloride, benzyltrimethylammonium chloride, benzyltributylammonium chloride, benzyl triphenyl phosphonium chloride, butyltriethyl ammonium bromide, butyltiphenylphosphonium bromide, cetyltrimethyl ammonium bromide, cetyltrimethyl ammonium chloride, ethyl triphenylphosphonium bromide, ethyltriphenylphosphonium iodide, methyltrioctyl ammonium bromide, methyltriphenylphosphonium bromide, methyltriphenylphosphonium iodide, phenyltrimethylammonium chloride, tetrabutylammonium hydroxide, tetrabutylammonium perchlorate, tetrabutylammonium bromide, tetrabutylammonium hydrogensulphate, tetrabutylammonium iodide, tetrabutylammonium tetrafluoroborate, tetrabutylammonium thiocyanate, tetraethylammonium hydroxide, tetraethylammonium iodide, tetramethylammonium chloride, tetraoctylammonium bromide, tetraphenylphosphonium bromide, tetrapropylammonium hydroxide, tetrapropylammonium bromide and tributylmethylammonium chloride.

Alternatively, the O-methylation can also be performed using a suitable methylating agent in the presence of an organometallic compound.

The organometallic compounds which may be used include organolithium compound. The organolithium compound may be an alkyl lithium compound, such as butyl lithium, methyl lithium or hexyl lithium, LDA, LHMDS or an aryl lithium compound such as phenyl lithium. In particular, t-butyllithium, and n-butyl lithium can be used. Alternatively, other organometallic compounds comprising a metal-carbon binding may be used. For example, organozinc compounds including organo zinc halide, organo aluminum compounds including organo aluminum halides, organo tin compounds including organo tin halides or organo magnesium compounds including organo magnesium halides (Grignard compounds), wherein, halides include Cl, Br and/or I and organo moiety may be an aryl or alkyl, for example, Grignard compounds Alkyl-Mg—Y, or Aryl-Mg—Y, wherein, Y is Cl, Br or/and I.

Suitable solvents used at this step may include one or more of THF, 2-methyl THF, 2-methoxyethyl ether mixtures or dimethoxymethane, and the like. In particular, THF may be used.

In general, the reaction may be carried from about 5 hours to about 18 hours at about 0-5° C. The reaction may be carried out at a higher or lower temperatures, for example between –19 and +25° C., and the reaction time may vary accordingly.

Suitable methylating agents which may be used for methylation include one or more of methyl iodide, dimethyl sulfate, trimethyl silyldiazomethane, and dimethylsulfoxide.

Suitable bases used in the process may include one or more of metal hydrides, hydroxides, oxides of metals such as hydrides, hydroxides, oxides of sodium, potassium, calcium, silver, and the like, and sodium methoxide.

The O-methylation can optionally be performed in the presence of a catalyst selected from suitable imidazoles, dimethylaminopyridine, and pyridine.

Suitable solvents used in this step may include one or more of polar organic solvents, tetrahydrofuran, methyl THF, dimethylsulfoxide, acetonitrile, and the like. The reaction may be carried out from about 2.5-5 hours at about –18° C. to –3° C. In particular, the reaction may be carried out for about 3-4 hours at about –15° C. to –5° C. The reaction may be performed at a higher or lower temperature such as any temperature between –20° C. to 0° C.

In another aspect, there is provided a novel intermediate of Formula (II) which can be used in the preparation of lacosamide, Formula (II)

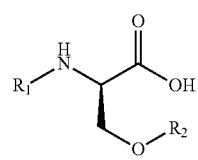

wherein $R_1$ is a suitable amino protecting group selected from Boc, Fmoc, Cbz, Tos, and the like; and $R_2$ is suitable hydroxyl protecting group selected from benzyl, tertiary butyl, benzoyl, and the like.

Particular useful compounds may be selected from:

Formula (VII)

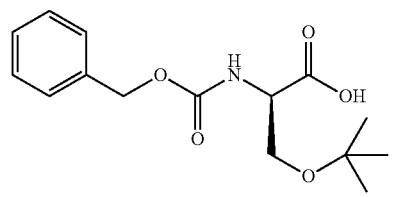

-continued

Formula (XI)

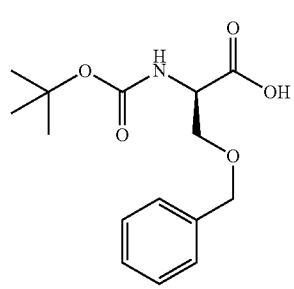

The inventors also have developed a process for the purification of lacosamide by obtaining a solution of lacosamide in one or more suitable solvents and recovering the pure lacosamide by removal of the solvents.

In one aspect, the process may include obtaining a solution of lacosamide in one or more solvents; adding an anti-solvent to the solution; and isolating the pure lacosamide by removing the solvents.

The lacosamide may be prepared according to the present invention or may be prepared by any of the methods known in the art including those described in U.S. Reissue Pat. No. RE 38,551 and US Patent Publication No. 20090143472; and International (PCT) Publication No. WO 2006/037574.

The term "solvent" includes one or more of ethyl acetate, n-hexane, toluene, DIPE, MTBE, THF, acetone, chloroform, DCM, methanol, ethanol, IPA, acetonitrile or mixtures thereof.

The purification may be carried out by obtaining a solution of lacosamide in one or more suitable solvents. In particular, the solution of lacosamide may be obtained in n-hexane, toluene, DIPE, or MTBE.

The purification is carried out by process includes obtaining a solution one or more solvents, adding an anti solvents to the solution, preferred solvents according to the invention are n-hexane, toluene, DIPE, or MTBE and anti solvents according to the invention are ethyl acetate, acetone, THF, chloroform, DCM, toluene, methanol, IPA, acetonitrile and the like.

The solution of lacosamide in a solvent can be obtained by dissolving, slurring, stirring, or a combination thereof. The solution of lacosamide may be obtained by heating the solvent. It may be heated from about 25° C. to reflux temperature.

The resultant solution can be clarified to remove foreign particulate matter or treated with activated charcoal to remove coloring and other related impurities.

The solvent may be removed by a technique which includes, for example, distillation, distillation under vacuum, evaporation, filtration, filtration under vacuum, decantation and centrifugation.

The product obtained may be further or additionally dried to achieve the desired moisture values. For example, the product may be further or additionally dried in a tray drier, dried under vacuum and/or in a Fluid Bed Drier.

The process may produce the pure lacosamide having purity more than 98.95% and a chiral purity more than 99.33% by HPLC. In particular, it may produce the pure lacosamide having purity more than 99.43% and chiral purity more than 99.72% by HPLC. In another embodiment, there is provided a novel process for the preparation of lacosamide using N—Z—O-tertbutyl-D-Serine. The process includes:

a) reacting N—Z—O-tert-butyl-D-serine of Formula VII,

Formula VII

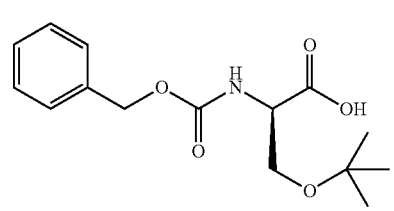

with benzyl amine in the presence of a suitable base and a suitable carboxylic acid activator to give N-benzyl-O-tert-butyl-$N^2$—Z-D-serinamide of Formula VIII;

Formula VIII

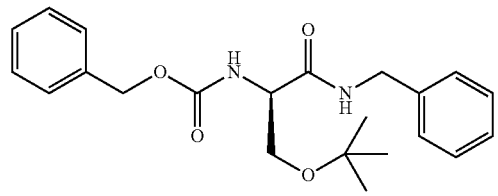

b) deprotecting the N-benzyl-O-tert-butyl-$N^2$—Z-D-serinamide of Formula VIII to give N-benzyl-O-tert-butyl-D-serinamide of Formula IX by addition of $H_2$/Pd—C;

Formula IX

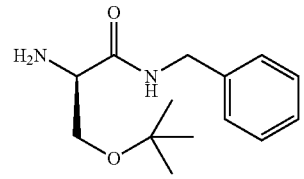

c) acetylating the N-benzyl-O-tert-butyl-D-serinamide of Formula IX to obtain N-benzyl-O-tert-butyl-$N^2$-acetyl-D-serinamide of Formula X;

Formula X

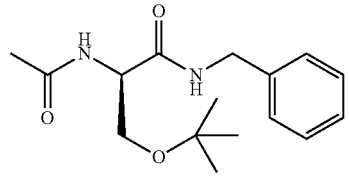

d) deprotecting the t-butyl group of Formula X using trifluoroacetic acid to obtain N-benzyl-$N^2$-acetyl-D-serinamide of Formula VI; and Formula VI

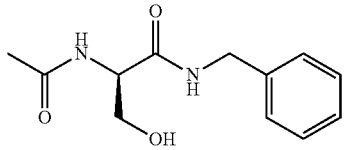

e) O-methylating the alcoholic group of compound of Formula VI to give lacosamide of Formula I.

The reaction conditions for step-(a) to (e) are as described here in above.

In yet another embodiment, there is provided a novel process for the preparation of lacosamide using N—Z—O-tert-butyl-D-Serine. The process includes:

a) reacting N-Boc-O-benzyl-D-serine of Formula XI,

Formula XI

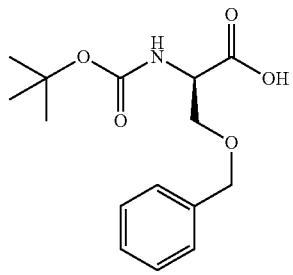

with benzyl amine in the presence of a suitable base and a suitable carbonyl activator to give N-benzyl-O-benzyl-N²-Boc-D-serinamide of Formula XII;

Formula XII

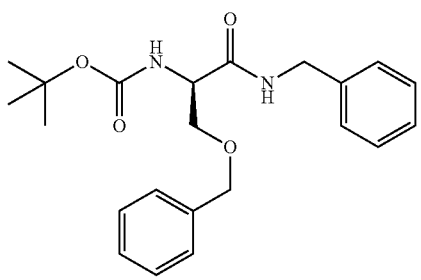

b) deprotecting the t-butyl group of Formula XII using trifluoroacetic acid to obtain N-benzyl-O-benzyl-D-serinamide of Formula XIII;

Formula XIII

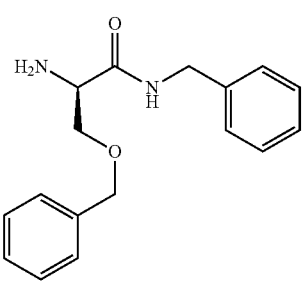

c) acetylating the N-benzyl-O-benzyl-N²-acetyl-D-serinamide of Formula XIII to obtain N-benzyl-O-benzyl-N²-acetyl-D-serinamide of Formula XIV;

Formula XIV

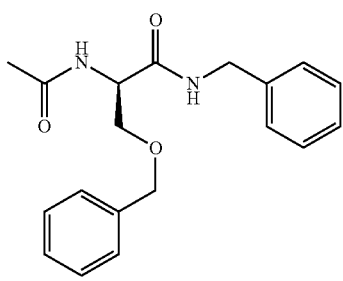

d) converting N-benzyl-O-benzyl-N²-acetyl-D-serinamide of Formula XIV to N-benzyl-N²-acetyl-D-serinamide of Formula VI by the addition of $H_2$/Pd—C; and Formula VI

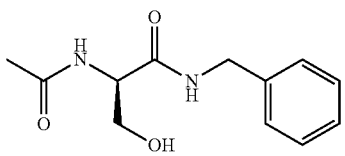

e) O-methylating the alcoholic group of compound of Formula VI to give lacosamide of Formula I.

The reaction conditions for step-(a) to (e) are as described here in above.

In another aspect there is provided a pharmaceutical composition that includes a therapeutically effective amount of pure lacosamide having purity more than 99% and chiral purity more than 99.8% by HPLC; and one or more pharmaceutically acceptable carriers, excipients or diluents.

Lacosamide may be formulated into ordinary dosage forms such as, for example, tablets, capsules, pills, solutions, etc. In these cases, the medicaments can be prepared by conventional methods with conventional pharmaceutical excipients.

Analytical Instruments/Techniques Used

The Purity by analytical HPLC at $\lambda_{max}$ 220 nm using column Phenomenex Luna, 250 mm×4.6 mm×5μ or its equivalent on SHIMADZU series under the following conditions, Detector: UV absorption photometer Wavelength: 220 nm
Column temp.: 30° C.
Flow rate: 1.0 mL/min. Injection Vol.: 5 μL
Mobile Phase: A. 10 Mm potassium dihydrogen phosphate buffer (pH between 4.6 to 4.7)
B. Acetonitrile (HPLC Grade)
Diluent: Water:Acetonitrile (50:50)

Chiral Purity were analyzed by analytical HPLC at $\lambda_{max}$ 220 nm using column Chiral-Cel OJ-H, 250 mm×4.6 mm×5μ or its equivalent on Shimadzu LCVP model under the following conditions, Detector: UV absorption photometer Wavelength: 220 nm
Column temp.: 30° C.
Flow rate: 0.8 mL/min. Injection Vol.: 5 μL
Mobile Phase: n-Hexane: 0.05% TFA in ETOH (92:08)

Melting points were taken on Mettler Toledo's FP90 Thermosystem.

Specific optical rotation (SOR) were taken on Jasco P-1030 polarimeter.

$^1$H NMR was taken on Bruker TOPSIN 2.0 400 MHz.
$^{13}$C NMR was taken on Bruker TOPSIN 2.0 100 MHz.

The infrared (IR) spectrum has been recorded on a Shimadzu FTIR-8400 model spectrophotometer, between 400 $cm^{-1}$ and 4000 $cm^{-1}$, with a resolution of 4 $cm^{-1}$ in a KBr pellet.

The Mass spectrum has been recorded on a Shimadzu LCMS 2010A model, between 50-200 m/z The invention is further illustrated by the following examples, which are provided merely to be exemplary of the invention and do not limit the scope of the invention. Certain modifications and equivalents will be apparent to those skilled in the art and are intended to be included within the scope of the invention.

Example 1

Preparation of N-benzyl-O-benzyl-N²-Boc-D-serinamide (XII)

To a cooled (−20° C.) solution of N-Boc-O-benzyl-D-serine (26 g) in tetrahydrofuran (208 mL), N-methylmorpholine (15 mL) was added and reaction mixture was stirred for 5 minutes. isobutylchloformate (18 mL) was added to the reaction mixture in 5 minutes at −20° C. The solution was further stirred for 5 minutes at −20° C. and benzyl amine (15.01 mL) was added to in it in 5 minutes at −20° C. The solution was stirred for 1 hr at −20° C. The solution was allowed to warm at room temperature and stirred for 1 hour. The precipitated hydrochloride salt of N-methylmorpholine was filtered. The filtrate was concentrated under vacuum to obtain solid 17 g N-benzyl-O-benzyl-N²-Boc-D-serinamide after crystallization from diisopropylether.
Yield: 17 g, HPLC Purity: 86.56%, Mass 407.23 (M+Na), % Yield: 50%.

Example 2

Preparation of N-benzyl-O-benzyl-N²-Boc-D-serinamide(XII)

To a cooled (−20° C.) solution of N-Boc-O-benzyl-D-serine (2.5 g) in ethylacetate (30 mL), N-methylmorpholine (1.1 mL) was added and reaction mixture stirred for 5 minutes and isobutylchloformate (1.2 mL) was added to the reaction mixture in 5 minutes at −20° C. The solution was stirred for 5 minutes at −20° C. and benzyl amine (1.1 mL) was added to the reaction mixture in 5 minutes at −20° C. The solution was stirred for 1 hr at −20° C. The solution was allowed to warm at room temperature and stirred for 1 hour. The hydrochloride salt of N-methylmorpholine was filtered. Organic layer was concentrated under vacuum to obtain solid 1.7 g N-benzyl-O-benzyl-N²-Boc-D-serinamide after crystallization by diisopropylether.
Yield: 1.7 g, HPLC Purity: 94.1%, % Yield: 50%

Example 3

Preparation of N-benzyl-O-benzyl-N²-Boc-D-serinamide(XII)

To a cooled (−20° C.) solution of N-Boc-O-benzyl-D-serine (1 g) in tetrahydrofuran (12 mL), N-methylmorpholine (0.44 mL) was added and stirred for 5 minutes and isobutylchloformate (0.48 mL) was added to it in 5 minutes at −20° C. The solution was stirred for 5 minutes at −20° C. and benzyl amine (0.44 mL) was added to the reaction mixture in 5 minutes at −20° C. The solution was stirred for 1 hr at −20° C. The solution was allowed to warm at room temperature and stirred for 1 hour. The hydrochloride salt of N-methylmorpholine was filtered. Organic layer was concentrated under vacuum to obtain solid 1.1 g N-benzyl-O-benzyl-N²-Boc-D-serinamide after crystallization by diisopropylether.
Yield: 1.1 g, HPLC Purity: 97.5%, % Yield: 85%

Example 4

Preparation of N-benzyl-O-benzyl-N²-Boc-D-serinamide(XII)

To a cooled (−20° C.) solution of N-Boc-O-benzyl-D-serine (1 g) in dichloro methane (12 mL), triethylamine (0.44 mL) was added and stirred for 5 minutes and subsequently isobutylchloformate (0.51 mL) was added to the reaction mixture in 5 minutes at −20° C. The solution was stirred for 5 minutes at −20° C. and benzyl amine (0.44 mL) was added to in it in 5 minutes at −20° C. The solution was stirred for 1 hr at −20° C. The solution was allowed to warm to room temperature and stirred for 1 hour. The hydrochloride salt of N-methylmorpholine was filtered. Organic layer was concentrated under vacuum to obtain solid, 0.53 g N-benzyl-O-benzyl-N²-Boc-D-serinamide after crystallization by diisopropylether.
Yield: 0.53 g, HPLC Purity: 89.4%, % Yield: 41%

Example 5

Preparation of N-benzyl-O-benzyl-N²-Boc-D-serinamide(XII)

To a cooled (−20° C.) solution of N-Boc-O-benzyl-D-serine (1 g) in dichloro methane (12 mL), N-methylmorpholine (0.44 mL) was added and stirred for 5 minutes and methylchloformate (0.51 mL) was added to the reaction mixture in 5 minutes at −20° C. The solution was stirred for 5 minutes at −20° C. and benzyl amine (0.44 mL) was added to in it in 5 minutes at −20° C. The solution was stirred for 1 hr at −20° C. The solution was allowed to warm at room temperature and stirred for 1 hour. The hydrochloride salt of N-methylmorpholine was filtered. Organic layer was concentrated under vacuum to obtain solid 0.64 g N-benzyl-O-benzyl-N²-Boc-D-serinamide after crystallization by diisopropylether.
Yield: 0.64 g, HPLC Purity: 87.1%, Mass 384.9 (M+H), % Yield: 49%

Example 6

Preparation of N-benzyl-O-benzyl-N²-Boc-D-serinamide(XII)

To a cooled (−20° C.) solution of N-Boc-O-benzyl-D-serine (25 g) in dichloro methane (300 mL). N-methylmorpholine (11.18 mL) was added and stirred for 5 minutes and isobutylchloformate (12.79 mL) was added to the reaction mixture in 5 minutes at −20° C. The solution was stirred for 5 minutes at −20° C. and benzyl amine (11.18 mL) was added to in it in 5 minutes at −20° C. The solution was stirred for 1 hr at −20° C. The solution was allowed to warm at room temperature and stirred for 1 hour. The hydrochloride salt of N-methylmorpholine was filtered. Organic layer was concentrated under vacuum to obtain solid 31 g N-benzyl-O-benzyl-N²-Boc-D-serinamide after crystallization by diisopropylether.
Yield: 31 g, HPLC Purity: 99.01%, MS=384.9 [M⁺+1,]; Yield=95%; $[\alpha]_D^{25}$ (c=1% in DMF)=−0.75°; ¹H NMR (DMSO-d⁶)=δ1.38 (s, $CH_3$—Boc), δ3.61 (m, $CH_2$O-benzyl), δ4.28 (m, CH), δ4.24 (m, $NHCH_2$Ph), δ4.47 (s, $OCH_2$Ph), δ6.89 (d, NHCH), δ7.17-7.34 (m $PhHCH_2$NH, $PhHCH_2$O) δ8.44 (t, $NHCH_2$Ph); ¹³C NMR (DMSO-d⁶) δ28.1 ($C(CH_3)_3$), δ41.0 ($NHCH_2$Ph), δ54.3 (CH), δ69.9 ($CH_2$O), δ72.0 ($OCH_2$Ph), δ78.2 ($C(CH_3)_3$), δ126.6-139.2 (Ph), δ155.2 (OC(O)NH), δ169.9 (C(O)NH); IR (KBr) 3338, 3306, 2976, 1701, 1656, 1552, 1527, 1496, 1452, 1365, 1273, 1251, 1124, 1057, 729, 696 cm$^{-1}$

Example 7

Preparation of N-benzyl-O-benzyl-D-serinamide(XIII)

To a solution of N-benzyl-O-benzyl-N$^2$-Boc-D-serinamide (16 g) and dichloromethane (80 mL), trifluoroacetic acid (80 mL) was added. The solution was stirred for 2 hours and the reaction was monitored for completion of reaction. The solution was concentrated under vacuum to obtain solid which was dissolved in water. The aqueous solution was basified to pH 8-10 with 5% sodium hydroxide and was extracted with ethyl acetate. The organic layer was separated and washed with a brine solution. The organic layer was concentrated under vacuum to obtain an oily residue 11 g of N-benzyl-O-benzyl-D-serinamide.
Yield: 11 g, HPLC Purity: 71.98%, Mass: 307.21 m/z (M+Na), % Yield: 93%.

Example 8

Preparation of N-benzyl-O-benzyl-D-serinamide(XIII)

To a solution of N-benzyl-O-benzyl-N$^2$-Boc-D-serinamide (1 g) and dichloromethane (5 mL), aq. HCl (35%) (5 mL) was added. The solution was stirred for 2 hours at room temperature for completion of reaction. The solution was concentrated under vacuum to remove dichloromethane and subsequently water was added. The aqueous layer was basified to pH 8-10 with 5% sodium hydroxide. The aqueous layer was extracted with ethyl acetate and the combined organic layer was washed with brine solution. Organic layer was concentrated under vacuum to obtain an oily residue 0.46 g of N-benzyl-O-benzyl-D-serinamide.
Yield: 0.46 g, HPLC Purity: 85.1%, % Yield: 62%

Example 9

Preparation of N-benzyl-O-benzyl-D-serinamide(XIII)

To a solution of N-benzyl-O-benzyl-N$^2$-Boc-D-serinamide (1 g) and dichloromethane (5 mL), aq. HCl (20%) (5 mL) was added. The solution was stirred for 2 hours at room temperature for completion of reaction. The solution was concentrated under vacuum to remove dichloromethane and subsequently water was added. The aqueous layer was basified to pH 8-10 with 5% sodium hydroxide. The aqueous layer was extracted with ethyl acetate and the combined organic layer was washed with brine solution. Organic layer was concentrated under vacuum to obtain an oily residue 0.33 g of N-benzyl-O-benzyl-D-serinamide.
Yield: 0.33 g, HPLC Purity: 79.2%, % Yield: 45%

Example 10

Preparation of N-benzyl-O-benzyl-D-serinamide(XIII)

To a solution of N-benzyl-O-benzyl-N$^2$-Boc-D-serinamide (1 g) and dichloromethane (5 mL), aq. HCl (10%) (5 mL) was added. The solution was stirred for 2 hours at room temperature for completion of reaction. The solution was concentrated under vacuum to remove dichloromethane and subsequently water was added. The aqueous was basified to pH 8-10 with 5% sodium hydroxide. The aqueous layer was extracted with ethyl acetate and the combined organic layers washed with brine solution. Organic layer was concentrated under vacuum to obtain an oily residue 0.22 g of N-benzyl-O-benzyl-D-serinamide.
Yield: 0.22 g, HPLC Purity: 75.1%, % Yield: 30%.

Example 11

Preparation of N-benzyl-O-benzyl-D-serinamide(XIII)

To a solution of N-benzyl-O-benzyl-N$^2$-Boc-D-serinamide (3 g) and dichloromethane (15 mL), trifluoroacetic acid (15 mL) was added. The solution was stirred for 2 hours at 40° C. for completion of reaction. The solution was concentrated under vacuum to remove solvents and subsequently water was added. The aqueous layer was basified to pH 8-10 with 5% sodium hydroxide. The aqueous layer was extracted with ethyl acetate and the combined organic layer was washed with brine solution. Organic layer was concentrated under vacuum to obtain an oily residue solidify by n-Hexane to give 1.55 g of N-benzyl-O-benzyl-D-serinamide.
Yield: 1.55 g, HPLC Purity: 86.3%, % Yield: 70%

Example 12

Preparation of N-benzyl-O-benzyl-D-serinamide(XIII)

To a solution of N-benzyl-O-benzyl-N$^2$-Boc-D-serinamide (30 g) and dichloromethane (150 mL), trifluoroacetic acid (150 mL) was added. The solution was stirred for 2 hours at room temperature for completion of reaction. The solution was concentrated under vacuum to obtain solid which was dissolved in water. The aqueous layer was basified to pH 8-10 with 5% sodium hydroxide. The aqueous layer was extracted with ethyl acetate and the combined organic layers washed with brine solution. Organic layer was concentrated under vacuum to obtain an oily residue solidify by n-Hexane to give 20 g of N-benzyl-O-benzyl-D-serinamide.
Yield: 20 g, HPLC Purity: 97.62%, MS=284.8 [M$^+$+1, 100], Yield=90%; [α]$_D^{25}$ (c=1% in DMF)=+0.16°; $^1$H NMR (DMSO-d$^6$)=δ3.44 (m, CH), δ3.54 (m CH$_2$O), δ4.28 (m, NHCH$_2$Ph), δ4.47 (s, OCH$_2$Ph), δ7.17-7.35 (m, PhH, PhH), δ8.42 (t, NHCH$_2$Ph); $^{13}$C NMR (DMSO-d$^6$) δ41.9 (NHCH$_2$Ph), δ54.8 (CH), δ72.1 (OCH$_2$Ph), δ73.0 (CH$_2$O), δ126.5-139.4 (Ph, Ph), δ173.0 (C(O)NH); IR (KBr) 3381, 3265, 3030, 2935, 2847, 1643, 1525, 1452, 1359, 1332, 1244, 1114, 1018, 734, 696 cm$^{-1}$

Example 13

Preparation of N-benzyl-O-benzyl-N$^2$-acetyl-D-serinamide(XIV)

To a clear solution of N-benzyl-O-benzyl-D-serinamide (10 g), 4-dimethylaminopyridine (214 mg) and dichloromethane (50 mL), acetic anhydride 4 mL were added at room temperature. The solution was stirred for 2 hours at room temperature. The dichloromethane layer was sequentially washed by water, 5% NaHCO$_3$ solution and brine solution to make neutral pH. The organic layer was concentrated under vacuum to obtain solid. 10 g N-benzyl-O-benzyl-N²-acetyl-D-serinamide after crystallization from diisopropylether.
Yield: 10 g, HPLC Purity: 95.75%, Mass: 327.24 m/z (M+H), 349.21 m/z (M+Na), % Yield: 87%.

Example 14

Preparation of N-benzyl-O-benzyl-N²-acetyl-D-serinamide(XIV)

To a clear solution of N-benzyl-O-benzyl-D-serinamide (1 g), 4-dimethylaminopyridine (0.021 g) and ethyl acetate (5 mL), acetic anhydride (0.34 mL) were added at room temperature. The solution was stirred for 2 hours at room temperature. The dichloromethane layer was sequentially washed by water, 5% NaHCO$_3$ solution, water and brine solution to make neutral pH. Organic layer was concentrated under vacuum to obtain solid 0.61 g N-benzyl-O-benzyl-N²-acetyl-D-serinamide after crystallization by diisopropylether.
Yield: 0.61 g, HPLC Purity: 89%, % Yield: 53%

Example 15

Preparation of N-benzyl-O-benzyl-N²-acetyl-D-serinamide(XIV)

To a clear solution of N-benzyl-O-benzyl-D-serinamide (1 g), 4-dimethylaminopyridine (0.0214 g), pyridine (5 mL) and acetic anhydride (0.34 mL) were added at room temperature. The solution was stirred for 2 hours at room temperature. The dichloromethane layer was sequentially washed by water, 5% NaHCO$_3$ solution, water and brine solution to make neutral pH. Organic layer was concentrated under vacuum to obtain solid 0.44 g N-benzyl-O-benzyl-N²-acetyl-D-serinamide after crystallization by diisopropylether.
Yield: 0.44 g, HPLC Purity: 86.5%, % Yield: 39%

Example 16

Preparation of N-benzyl-O-benzyl-N²-acetyl-D-serinamide(XIV)

To a clear solution of N-benzyl-O-benzyl-D-serinamide (1 g), pyridine (0.02 g), dichloromethane (5 mL) and acetic anhydride (0.34 mL) were added at room temperature. The solution was stirred for 2 hours at room temperature. The dichloromethane layer was sequentially washed by water, 5% NaHCO$_3$ solution, water and brine solution to make neutral pH. Organic layer was concentrated under vacuum to obtain solid 0.41 g N-benzyl-O-benzyl-N²-acetyl-D-serinamide after crystallization by diisopropylether.
Yield: 0.41 g, HPLC Purity: 84.2%, % Yield: 36%

Example-17

Preparation of N-benzyl-N²-acetyl-D-serinamide(XIV)

To a clear solution of N-benzyl-O-benzyl-D-serinamide (19 g), 4-dimethylaminopyridine (0.407 g), dichloromethane (95 mL) and acetic anhydride (7.57 mL) were added at room temperature. The solution was stirred for 2 hours at room temperature. The dichloromethane layer was sequentially washed by water, 5% NaHCO$_3$ solution, water and brine solution to make neutral pH. Organic layer was concentrated under vacuum to obtain solid 21 g N-benzyl-O-benzyl-N²-acetyl-D-serinamide after crystallization by diisopropylether.
Yield: 21 g, HPLC Purity: 99.80%, MS=326.9 [M⁺+1, 100], Yield=96%; [α]$_D^{25}$ (c=1% in DMF)=+0.04°; M.P=149.2° C.;
$^1$H NMR (DMSO-d$^6$)=δ1.8 (s, C(O)CH$_3$), δ3.60 (m, CH$_2$O), δ4.29 (d, NHCH$_2$Ph), δ4.48 (s, OCH$_2$Ph), δ4.53 (m, CH), δ7.16-7.35 (m, Ph, Ph), δ8.09 (d, C(O)NH), δ8.51 (t, NHCH$_2$Ph); $^{13}$C NMR (DMSO-d$^6$) δ22.5 (C(O)CH$_3$), δ42.0 (NHCH$_2$Ph), δ53.3 (CH), δ70.0 (CH$_2$O), δ 72.0 (OCH$_2$Ph), δ126.6-139.2 (m, Ph, Ph), δ169.3 (C(O)CH3 or C(O)NH), δ169.7 (C(O)CH$_3$ or C(O)NH); IR (KBr) 3292, 3090, 3063, 2856, 1635, 1533, 1454, 1311, 1240, 1028, 736, 696 cm$^{-1}$.

Example-18

Preparation of N-benzyl-N²-acetyl-D-serinamide(VI)

10% Palladium charcoal (1.8 g) was charged to a solution of N-benzyl-O-benzyl-N²-acetyl-D-serinamide (9 g) in methanol (90 mL). The reaction mixture was stirred for 2 hours under hydrogen pressure led to complete conversion. After completion of the reaction, the catalyst was filtered and the filtrate was concentrate under vacuum to obtain solid 6.0 g N-benzyl-N²-acetyl-D-serinamide after crystallization from diisopropylether
Yield: 6.0 g, HPLC Purity: 95.06%, Mass: 259.29 m/z (M+Na), % Yield: 92%

Example-19

Preparation of N-benzyl-N²-acetyl-D-serinamide(VI)

10% Palladium charcoal (1 g) was charged to a solution N-benzyl-O-benzyl-N²-acetyl-D-serinamide (5 g) in ethanol (115 mL). The reaction mixture was stirred for 2 hours under hydrogen pressure led to complete conversion. After completion of the reaction, the catalyst was filtered and the filtrate was concentrate under vacuum to obtain solid 2.6 g N-benzyl-N²-acetyl-D-serinamide. After crystallization by diisopropylether
Yield: 2.6 g, HPLC Purity: 89%, % Yield: 72%.

Example-20

Preparation of N-benzyl-N²-acetyl-D-serinamide(VI)

5% Palladium charcoal (0.4 g) was charged to a solution N-benzyl-O-benzyl-N²-acetyl-D-serinamide (1 g) in methanol (23 mL). The reaction mixture was stirred for 2 hours under hydrogen pressure led to complete conversion. After completion of the reaction, the catalyst was filtered and the filtrate was concentrate under vacuum to obtain solid 0.34 g N-benzyl-N²-acetyl-D-serinamide. After crystallization by diisopropylether
Yield: 0.34 g, HPLC Purity: 85.5%, % Yield: 47%.

Example-21

Preparation of N-benzyl-N²-acetyl-D-serinamide(VI)

10% Palladium charcoal (0.2 g) was charged to a solution N-benzyl-O-benzyl-N²-acetyl-D-serinamide (1 g) in methanol (23 mL) and acetic acid (5 mL). Subsequent stirring and hydrogenation for 2 hrs at room temperature led to complete conversion. After completion of the reaction, the catalyst was filtered and the filtrate was concentrate under vacuum to obtain solid 0.55 g N-benzyl-N²-acetyl-D-serinamide. After crystallization by diisopropylether
Yield: 0.55 g, HPLC Purity: 94%, % Yield: 76%.

Example-22

Preparation of N-benzyl-N²-acetyl-D-serinamide(VI)

10% Palladium charcoal (0.2 g) was charged to a solution N-benzyl-O-benzyl-N²-acetyl-D-serinamide (1 g) in methanol (10 mL). The reaction mixture was stirred for 2 hours under hydrogen pressure led to complete conversion. After completion of the reaction, the catalyst was filtered and the filtrate was concentrate under vacuum to obtain solid 0.65 g N-benzyl-N²-acetyl-D-serinamide. After crystallization by diisopropylether
Yield: 0.65 g, HPLC Purity: 93.1%, % Yield: 90%.

Example-23

Preparation of N-benzyl-N²-acetyl-D-serinamide(VI)

10% Palladium charcoal (0.2 g) was charged to a solution N-benzyl-O-benzyl-N²-acetyl-D-serinamide (1 g) in methanol (23 mL). The reaction mixture was stirred for 2 hours under hydrogen pressure at 40° C. After completion of the reaction, the catalyst was filtered and the filtrate was concentrate under vacuum to obtain solid 0.45 g N-benzyl-N²-acetyl-D-serinamide. After crystallization by diisopropylether
Yield: 0.45 g, HPLC Purity: 92.11%, % Yield: 62%

Example-24

Preparation of N-benzyl-N²-acetyl-D-serinamide(VI)

10% Palladium charcoal (4 g) was charged to a solution N-benzyl-O-benzyl-N²-acetyl-D-serinamide (20 g) in methanol (460 mL). The reaction mixture was stirred for 2 hours under hydrogen pressure led to complete conversion. After completion of the reaction, the catalyst was filtered and the filtrate was concentrate under vacuum to obtain solid 14.2 g N-benzyl-N²-acetyl-D-serinamide. After crystallization by diisopropylether
Yield: 14.2 g, HPLC Purity: 99.32%, MS=236.8 [M⁺+1, 100]
Yield: 98% mp=148.1° C.; $[\alpha]_D^{25}$ (c=1% in DMF)=+6.29°; NMR (DMSO-d⁶) δ1.86 (s, C(O)CH₃), δ3.57 (m, CH₂OH), δ4.26-4.30 (m, NHCH₂ and CH), δ4.89 (s, CH₂OH), δ7.18-7.30 (m, PhH), δ7.90 (d, C(O)NH), δ8.36 (t, NHCH₂Ph); ¹³C NMR (DMSO-d⁶) δ22.6 (C(O)CH₃), δ42.0 (CH₂Ph), δ55.3 (CH), δ61.7 (CH₂O), δ126.6 (C₄'), δ127.0 (2C₂' or 2C₃'), δ128.2' (2C₂' or 2C₃'), δ139.4 (C₁'), δ169.4 (C(O)CH₃ or C(O)NH), δ170.3 (C(O)CH₃ or C(O)NH); IR (KBr) 3325, 3194, 3088, 2931, 1654, 1637, 1560, 1465, 1431, 1379, 1298, 1249, 1153, 1053, 731 cm⁻¹.

Example-25

Preparation of N-benzyl-O-methyl-N²-acetyl-D-serinamide, Lacosamide

To a solution of dichloromethane (20 mL) and N-benzyl-N²-acetyl-D-serinamide (2 g) tetrabutylammonium bromide (273 mg) was added followed by the addition of 20% NaOH solution (1.69 mL) at room temperature. Dimethylsulphate (3.3 mL) and 50% NaOH (3.04 mL) were added. The solution was stirred for 3 hours at room temperature. The organic layer was separated and sequentially washed with water and brine solution. The organic layer was concentrated under vacuum to obtain solid 2.0 g lacosamide after crystallization from diisopropylether.
Yield: 2.0 g, HPLC Purity: 50.79%, Mass: 273.22 m/z (M+Na), % Yield: 94%.
Lacosamide (2.0 g) obtained above was dissolved in Toluene (20 mL) at a temperature from 80° C. to reflux temperature. The reflux temperature was maintained for 1 hr, and cooled to get solid. The solid so obtained was filtered and washed with diisopropylether to get white solid lacosamide 0.6 g.
Yield 0.6 g, HPLC Purity: 97.28%, Chiral Purity: 100%, Mass 273.22 m/z (M+Na)
Specific Optical Rotation (c=1, MeOH)=+15.60°, M.P: 141.5° C.

Example-26

Preparation of N-benzyl-O-methyl-N²-acetyl-D-serinamide, Lacosamide

To a solution of toluene (20 mL) and N-benzyl-N²-acetyl-D-serinamide (1.0 g) tetrabutylammonium bromide (0.068 g) was added followed by 20% NaOH (0.92 mL) at room temperature. Subsequently, dimethylsulphate (1.63 mL) and 50% NaOH (1.45 mL) were added. The solution was stirred for 3 hours at room temperature. Organic layer was separated and washed by water. Organic layer was concentrated under vacuum to obtain solid 0.6 g Lacosamide after crystallization by diisopropylether.
Crude compound (0.6 g) was stirred with mixture of Toluene: Ethyl acetate 1:1 (17.7 mL) for one hour at for one hour at room temperature, filter to get white solid compound 0.28 g.
HPLC Purity: 95.6%, Mass 250.9 (M+H), % Yield: 26%.

Example-27

Preparation of N-benzyl-O-methyl-N²-acetyl-D-serinamide, Lacosamide

To a solution of dichloromethane (10 mL) and N-benzyl-N²-acetyl-D-serinamide (0.5 g) tetrabutylammonium bromide (0.0345 g) was added followed by 20% NaOH (0.47 mL) at room temperature. Subsequently, dimethylsulphate (0.96 mL, 5 m.eq.) and 50% NaOH (0.76 mL) were added. The solution was stirred for 3 hours at room temperature. Organic layer was separated and washed by water. Organic layer was concentrated under vacuum to obtain solid 0.3 g Lacosamide after crystallization by diisopropyl ether.
Crude compounds (0.3 g) was refluxed with Toluene (0.75 mL) and get clear solution, to that Ethyl acetate (0.75 mL) was added at room temperature. Stir for one hour at for one hour at room temperature, filter to get white solid compound 0.16 g.
Yield 0.16 g, % Yield: 30%, HPLC Purity: 97.22%, Mass 251.1 (M+H).

Example-28

Preparation of N-benzyl-O-methyl-N²-acetyl-D-serinamide, Lacosamide

To a solution of dichloromethane (20 mL) and N-benzyl-N²-acetyl-D-serinamide (1 g) tetrabutylammonium bromide (0.069 g) was added followed by 20% NaOH (0.93 mL) at room temperature. Subsequently, dimethylsulphate (0.41 mL, 1 m.eq.) and 50% NaOH (1.52 mL) were added. The solution was stirred for 3 hours at room temperature. Organic layer was separated and washed by water. Organic layer was concentrated under vacuum to obtain solid 0.4 g Lacosamide after crystallization by diisopropylether.

Crude compounds (0.4 g) was refluxed with Toluene (10 mL) and get clear solution, to that Ethyl acetate (5 mL) was added at room temperature. Stir for one hour at for one hour at room temperature, filter to get white solid compound 0.26 g.

Yield 0.26 g, % Yield: 25%, HPLC Purity: 80.1%.

Example-29

Preparation of N-benzyl-O-methyl-$N^2$-acetyl-D-serinamide, Lacosamide

To a solution of dichloromethane (40 mL) and N-benzyl-$N^2$-acetyl-D-serinamide (2 g) tetrabutylammonium bromide (0.026 g, 0.01 m.eq.) was added followed by 20% NaOH (1.86 mL) at room temperature. Subsequently, dimethylsulphate (3.28 mL) and 50% NaOH (3 mL) were added. The solution was stirred for 13 hours at room temperature. Organic layer was separated and washed by water. Organic layer was concentrated under vacuum to obtain solid 0.75 g Lacosamide after crystallization by diisopropylether.

Crude compound (0.75 g) was stirred with mixture of Toluene:Ethyl acetate 1:1 (18.75 mL) for one hour at for one hour at room temperature, filter to get white solid compound 0.26 g.

Yield 0.26 g, % Yield: 12%, HPLC Purity: 87.11%.

Example-30

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.136 g, 0.1 m.eq.) was added followed by 20% NaOH (0.93 mL) at room temperature. Subsequently, dimethylsulphate (1.64 mL) and 50% NaOH (1.52 mL) were added. The solution was stirred for 3 hours at room temperature. Organic layer was separated and washed by water. Organic layer was concentrated under vacuum to obtain solid 0.55 g Lacosamide after crystallization by diisopropylether.

Crude compound (0.55 g) was stirred with mixture of Toluene:Ethyl acetate 1:1 (13.75 mL) for one hour at for one hour at room temperature, filter to get white solid compound 0.21 g.

Yield 0.21 g, % Yield: 20%, HPLC Purity: 93.2%.

Example-31

Preparation of N-benzyl-O-methyl-$N^2$-acetyl-D-serinamide, Lacosamide

To a solution of dichloromethane (0.3 mL, 3 vol.) and N-benzyl-$N^2$-acetyl-D-serinamide (0.1 g) tetrabutylammonium bromide (0.007 g) was added followed by 20% NaOH (0.009 mL) at room temperature. Subsequently, dimethylsulphate (0.16 mL) and 50% NaOH (0.15 mL) were added. The solution was stirred for 3 hours at room temperature. Organic layer was separated and washed by water. Organic layer was concentrated under vacuum to obtain solid 0.03 g Lacosamide after crystallization by diisopropylether.

Crude compound (0.03 g) was stirred with mixture of Toluene:Ethyl acetate 1:1 (0.75 mL) for one hour at for one hour at room temperature, filter to get white solid compound 0.015 g.

Yield 0.015 g, % Yield: 14%, HPLC Purity: 81.2%.

Example-32

Preparation of N-benzyl-O-methyl-$N^2$-acetyl-D-serinamide, Lacosamide

To a solution of dichloromethane (15 mL, 10 vol) and N-benzyl-$N^2$-acetyl-D-serinamide (1.5 g) tetrabutylammonium bromide (0.104 g) was added followed by 20% NaOH (1.4 mL) at room temperature. Subsequently, dimethylsulphate (2.46 mL) and 50% NaOH (2.28 mL) were added. The solution was stirred for 4 hours at room temperature. Organic layer was separated and washed by water. Organic layer was concentrated under vacuum to obtain solid 0.7 g Lacosamide after crystallization by diisopropylether.

Crude compound (0.7 g) was stirred with mixture of Toluene:Ethyl acetate 1:1 (17.5 mL) for one hour at for one hour at room temperature, filter to get white solid compound 0.5 g.

Yield 0.5 g, % Yield: 31%, HPLC Purity: 94.1%.

Example-33

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (4.23 mL, 5 m.eq.) at room temperature. Subsequently, dimethylsulphate (1.64 mL) and 50% NaOH (1.52 mL) were added. The solution was stirred for 3 hours at room temperature. Organic layer was separated and washed by water. Organic layer was concentrated under vacuum to obtain solid 0.54 g Lacosamide after crystallization by diisopropylether.

Crude compound (0.54 g) was stirred with mixture of Toluene:Ethyl acetate 1:1 (13.5 mL) for one hour at for one hour at room temperature, filter to get white solid compound 0.19 g.

Yield 0.19 g, % Yield: 18%, HPLC Purity: 92.1%.

Example-34

Preparation of N-benzyl-O-methyl-$N^2$-acetyl-D-serinamide, Lacosamide

To a solution of dichloromethane (22 mL) and N-benzyl-$N^2$-acetyl-D-serinamide (1.1 g) tetrabutylammonium bromide (0.076 g) was added followed by 20% NaOH (9.41 mL, 10 m.eq.) at room temperature. Subsequently, dimethylsulphate (1.80 mL) and 50% NaOH (1.67 mL) were added. The solution was stirred for 3 hours at room temperature. Organic layer was separated and washed by water. Organic layer was concentrated under vacuum to obtain solid 0.31 g Lacosamide after crystallization by diisopropylether.

Crude compound (0.31 g) was stirred with mixture of Toluene:Ethyl acetate 1:1 (7.7 mL) for one hour at for one hour at room temperature, filter to get white solid compound 0.15 g. Yield 0.15 g, % Yield: 14%, HPLC Purity: 89.12%.

Example-35

Preparation of N-benzyl-O-methyl-$N^2$-acetyl-D-serinamide, Lacosamide

To a solution of dichloromethane (4 mL) and N-benzyl-$N^2$-acetyl-D-serinamide (0.2 g) tetrabutylammonium bromide (0.014 g) was added followed by 5% NaOH (0.74 mL, 1.1 m.eq.) at room temperature. Subsequently, dimethylsulphate (0.328 mL) and 50% NaOH (0.30 mL) was added. The solution was stirred for 10 hours at room temperature. Organic layer was separated and washed by water. Organic layer was concentrated under vacuum to obtain solid 0.1 g Lacosamide after crystallization by diisopropylether.
Crude compound (0.1 g) was stirred with mixture of Toluene:Ethyl acetate 1:1 (2.5 mL) for one hour at for one hour at room temperature, filter to get white solid compound 0.04 g. Yield 0.04 g, % Yield: 19%, HPLC Purity: 93.5%.

Example-36

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 10% NaOH (0.186 mL, 1.1 m.eq.) at room temperature. Subsequently, dimethylsulphate (0.16 mL) and 50% NaOH (0.15 mL) was added. The solution was stirred for 10 hours at room temperature. Organic layer was separated and washed by water. Organic layer was concentrated under vacuum to obtain solid 0.05 g Lacosamide after crystallization by diisopropylether.
Crude compound (0.05 g) was stirred with mixture of Toluene:Ethyl acetate 1:1 (1.25 mL) for one hour at for one hour at room temperature, filter to get white solid compound 0.026 g.
Yield 0.026 g, % Yield: 25%, HPLC Purity: 95.11%.

Example-37

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 30% NaOH (0.062 mL, 1.1 m.eq.) at room temperature. Subsequently, dimethylsulphate (0.164 mL) and 50% NaOH (0.15 mL) was added. The solution was stirred for 10 hours at room temperature.
Organic layer was separated and washed by water. Organic layer was concentrated under vacuum to obtain solid 0.06 g Lacosamide after crystallization by diisopropylether.
Crude compound (0.06 g) was stirred with mixture of Toluene:Ethyl acetate 1:1 (1.5 mL) for one hour at for one hour at room temperature, filter to get white solid compound 0.028 g. Yield 0.028 g, % Yield: 26%, HPLC Purity: 96.5%.

Example-38

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 50% NaOH (0.037 mL, 1.1 m.eq.) at room temperature. Subsequently, dimethylsulphate (0.16 mL) and 50% NaOH (0.15 mL) were added. The solution was stirred for 10 hours at room temperature. Organic layer was separated and washed by water. Organic layer was concentrated under vacuum to obtain solid 0.03 g Lacosamide after crystallization by diisopropylether.
Crude compound (0.03 g) was stirred with mixture of Toluene:Ethyl acetate 1:1 (0.75 mL) for one hour at for one hour at room temperature, filter to get white solid compound 0.011 g.
Yield 0.011 g, % Yield: 10%, HPLC Purity: 89.1%.

Example-39

Preparation of N-benzyl-O-methyl-$N^2$-acetyl-D-serinamide, Lacosamide

To a solution of dichloromethane (4 mL) and N-benzyl-$N^2$-acetyl-D-serinamide (0.2 g) tetrabutylammonium bromide (0.014 g) was added followed by 20% NaOH (0.19 mL) at room temperature. Subsequently, dimethylsulphate (0.33 mL) and 50% NaOH (0.67 mL, 10 m.eq.) were added. The solution was stirred for 3 hours at room temperature. Organic layer was separated and washed by water. Organic layer was concentrated under vacuum to obtain solid 0.1 g Lacosamide after crystallization by diisopropylether.
Crude compound (0.1 g) was stirred with mixture of Toluene:Ethyl acetate 1:1 (2.5 mL) for one hour at for one hour at room temperature, filter to get white solid compound 0.05 g.
Yield 0.05 g, % Yield: 24%, HPLC Purity: 62.1%

Example-40

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 20% NaOH (0.093 mL) at room temperature. Subsequently, dimethylsulphate (0.16 mL) and 50% NaOH (0.033 mL, 1 m.eq.) were added. The solution was stirred for 3 hours at room temperature. Organic layer was separated and washed by water. Organic layer was concentrated under vacuum to obtain solid 0.06 g Lacosamide after crystallization by diisopropylether.
Crude compound (0.06 g) was stirred with mixture of Toluene:Ethyl acetate 1:1 (1.5 mL) for one hour at for one hour at room temperature, filter to get white solid compound 0.022 g.
Yield 0.022 g, % Yield: 21%, HPLC Purity: 49.5%.

Example-41

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 20% NaOH (0.093 mL) at room temperature. Subsequently, dimethylsulphate (0.164 mL) and 5% NaOH (3.04 mL) were added. The solution was stirred for 3 hours at room temperature. Organic layer was separated and washed by water (2 mL). Organic layer was concentrated under vacuum to obtain solid 0.041 g Lacosamide after crystallization by diisopropylether.

Crude compound (0.041 g) was stirred with mixture of Toluene:Ethyl acetate 1:1 (1.03 mL) for one hour at for one hour at room temperature, filter to get white solid compound 0.02 g.
Yield 0.02 g, % Yield: 19%, HPLC Purity: 90.66%.

Example-42

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 20% NaOH (0.093 mL) at room temperature. Subsequently, dimethylsulphate (0.164 mL) and 10% NaOH (1.52 mL) were added. The solution was stirred for 3 hours at room temperature. Organic layer was separated and washed by water. Organic layer was concentrated under vacuum to obtain solid 0.05 g Lacosamide after crystallization by diisopropylether.
Crude compound (0.05 g) was stirred with mixture of Toluene:Ethyl acetate 1:1 (1.25 mL) for one hour at for one hour at room temperature, filter to get white solid compound 0.03 g.
Yield 0.03 g, % Yield: 28%, HPLC Purity: 95.12%.

Example-43

Preparation of N-benzyl-O-methyl-$N^2$-acetyl-D-serinamide, Lacosamide

To a solution of dichloromethane (2 mL) and N-benzyl-$N^2$-acetyl-D-serinamide (0.1 g) tetrabutylammonium bromide (0.007 g) was added followed by 20% NaOH (0.093 mL) at room temperature. Subsequently, dimethylsulphate (0.164 mL) and 30% NaOH (0.05 mL) were added. The solution was stirred for 3 hours at room temperature. Organic layer was separated and washed by water. Organic layer was concentrated under vacuum to obtain solid 0.061 g Lacosamide after crystallization by diisopropylether.
Crude compound (0.061 g) was stirred with mixture of Toluene:Ethyl acetate 1:1 (1.52 mL) for one hour at for one hour at room temperature, filter to get white solid compound 0.025 g.
Yield 0.025 g, % Yield: 39%, HPLC Purity: 94.9%.

Example-44

Preparation of N-benzyl-O-methyl-$N^2$-acetyl-D-serinamide, Lacosamide

To a solution of dimethyl sulfoxide (2.5 mL) and N-benzyl-$N^2$-acetyl-D-serinamide (0.1 g) was added followed by 50% KOH (1.25 mL) at room temperature. Dimethylsulphate (0.02 mL) and 10% KOH (0.12 mL) were added. The solution was stirred for 16 hours at room temperature. Reaction mixture was dumped in to the water and product extracted by dichloromethane. Organic layer was separated and washed by water. Organic layer was concentrated under vacuum to obtain solid 0.051 g Lacosamide after crystallization by diisopropylether.
Crude compound (0.051 g) was stirred with mixture of Toluene:Ethyl acetate 1:1 (1.28 mL) for one hour at for one hour at room temperature, filter to get white solid compound 0.02 g.
Yield 0.02 g, % Yield: 19%, HPLC Purity: 82.2%.

Example-45

Preparation of N-benzyl-O-methyl-$N^2$-acetyl-D-serinamide, Lacosamide

To a solution of acetonitrile (2 mL) and N-benzyl-$N^2$-acetyl-D-serinamide (0.1 g) methyl iodide (0.069 g) was added at 0 to 5° C. Subsequently, silver dioxide (0.2 g) was added. The solution was stirred for 19 hours at room temperature. The solid obtained was filtered and filtrate was distilled out, and then dump in to water and compound was extracted by dichloromethane. Organic layer was separated and washed by water. Organic layer was concentrated under vacuum to obtain solid 0.045 g Lacosamide after crystallization by diisopropylether purified by toluene:ethyl acetate (1:1).
Yield 0.023 g, % Yield: 22%, HPLC Purity: 85.5%.

Example-46

Preparation of N-benzyl-O-methyl-$N^2$-acetyl-D-serinamide, Lacosamide

To a solution of tetrahydrofuran (2 mL) and N-benzyl-$N^2$-acetyl-D-serinamide (0.1 g) added followed methyl iodide (0.3 mL) at 0 to 5° C. Subsequently, sodium hydride (0.05 g) was added at same temperature. The solution was stirred for 3 hours at room temperature. The reaction mixture was dumped in to the water and product was extracted by dichloromethane. Organic layer was separated and washed by water. Organic layer was concentrated under vacuum to obtain solid 0.06 g Lacosamide after crystallization by diisopropylether.
Crude compound (0.06 g) was stirred with mixture of Toluene:Ethyl acetate 1:1 (1.5 mL) for one hour at for one hour at room temperature, filter to get white solid compound 0.022 g.
Yield 0.022 g, % Yield: 21%, HPLC Purity: 83.3%

Example-47

Preparation of N-benzyl-O-methyl-$N^2$-acetyl-D-serinamide, Lacosamide

To a solution of dichloromethane (280 mL) and N-benzyl-$N^2$-acetyl-D-serinamide (13.9 g) tetrabutylammonium bromide (0.94 g) was added and followed by 20% NaOH (12.9 mL) at room temperature. Subsequently, dimethylsulphate (22.82 mL) and 50% NaOH (21.17 mL) were added. The solution was stirred for 18 hours at room temperature. Organic layer was separated and sequentially washed by water, 5% citric acid solution, and brine solution. Organic layer was concentrated under vacuum to obtain solid 10.1 g Lacosamide after crystallization by diisopropylether.
Yield: 10.1 g, HPLC Purity: 95.10%, Mass: 250.8 m/z (M+H), % Yield: 69%,
Crude compound (10.1 g) was stirred with the mixture of Toluene:Ethyl acetate 1:1 (252.5 mL) at room temperature for 0.5 hr, filter the solid, this solid was washed with diisopropylether (100 mL) to get white solid Lacosamide 5.9 g.
Yield 5.9 g, % Yield: 40%, HPLC Purity: 98.83%, Chiral Purity: 99.55%, Mass 250.8 m/z [$M^+$+1, 100]; Specific Optical Rotation (c=1, MeOH)=+15.95°, M.P: 143.5° C., IR (KBr) 3290, 3086, 2924, 2883, 2806, 1635, 1546, 1454, 1138, 694 $cm^{-1}$;

$^1$H NMR (DMSO-D$^6$) δ1.8 (s, C(O)CH$_3$), δ3.24 (s, OCH$_3$), δ3.49 (m, CH$_2$OCH$_3$), δ4.28 (d, J=6.0 Hz, NHCH$_2$), δ4.45-4.50 (m, CH), δ8.09 (d, J=8.4 Hz, NH), δ8.48 (t, J=5.8 Hz, NHCH$_2$Ph), δ7.19-7.31 (m, PhH).
$^{13}$C NMR (DMSO-D$^6$), δ22.5 (C(O)CH$_3$), δ42.0 (CH$_2$NH), δ52.6 (CH), δ58.1 (OCH$_3$), δ72.1 (CH$_2$OCH$_3$), δ126.6 (C$_4$'), δ126.9 (2C$_2$' or 2C$_3$'), δ128.1 (2C$_2$' or 2C$_3$'), δ139.2 (C$_1$'), δ169.3 (C(O)CH$_3$ or C(O)NH), δ169.7 (C(O)CH$_3$ or C(O)NH) ppm; MS 250.8; Anal. (C$_{13}$H$_{18}$N$_2$O$_3$) C, H, N.

Example 47

Preparation of N-benzyl-O-tert-butyl-N$^2$—Z-D-serinamide (VIII)

To a cooled (–20° C.) solution of N—Z—O-tert-butyl-D-serine (15 g) in tetrahydrofuran (120 mL), N-methylmorpholine (8.24 mL) was added and stirred for 5 minutes and subsequently, isobutylchloformate (9.8 mL) was added in 5 minutes at –20° C. The solution was stirred for 5 minutes at –20° C. and benzyl amine (8.24 mL) was added to the reaction mixture in 5 minutes at –20° C. The solution was stirred for 45 minutes at –20° C. The solution was allowed to warm at room temperature and stirred for 1 hour. The hydrochloride salt of N-methylmorpholine was filtered. Organic layer was concentrated under vacuum to obtain solid 18.52 g N-benzyl-O-tert-butyl-N$^2$—Z-D-serinamide after crystallization by diisopropylether.
Yield: 18.52 g, HPLC Purity: 99.67%, Mass 385.19 (M+H), % Yield: 95%

Example 48

Preparation of N-benzyl-O-tert-butyl-N$^2$—Z-D-serinamide(VIII)

To a cooled (–20° C.) solution of N—Z—O-tert-butyl-D-serine (1.5 g) in ethylacetate (12 mL), N-methylmorpholine (0.82 mL) was added and stirred for 5 minutes and isobutylchloformate (0.98 mL) was added in 5 minutes at –20° C. The solution was stirred for 5 minutes at –20° C. and benzyl amine (0.82 mL) was added to the reaction mixture in 5 minutes at –20° C.' The solution was stirred for 45 minutes at –20° C. The solution was allowed to warm at room temperature and stirred for 1 hour. The hydrochloride salt of N-methylmorpholine was filtered. Organic layer was concentrated under vacuum to obtain solid 1 g N-benzyl-O-tert-butyl-N$^2$—Z-D-serinamide after crystallization by diisopropylether. HPLC Purity: 95%, Mass 385.4 (M+H), % Yield: 51%

Example 49

Preparation of N-benzyl-O-tert-butyl-N$^2$—Z-D-serinamide(VIII)

To a cooled (–20° C.) solution of N—Z—O-tert-butyl-D-serine (1 g) in dichloro methane (8 mL), N-methylmorpholine (0.54 mL) was added and stirred for 5 minutes and isobutylchloformate (0.64 mL) was added in 5 minutes at –20° C. The solution was stirred for 5 minutes at –20° C. and benzyl amine (0.54 mL) was added to the reaction mixture in 5 minutes at –20° C. The solution was stirred for 45 minutes at –20° C. The solution was allowed to warm at room temperature and stirred for 1 hour. The hydrochloride salt of N-methylmorpholine was filtered. Organic layer was concentrated under vacuum to obtain solid 0.7 g N-benzyl-O-tert-butyl-N$^2$—Z-D-serinamide after crystallization by diisopropylether. HPLC Purity: 93%, Mass 385.17 (M+H), % Yield: 54%.

Example 50

Preparation of N-benzyl-O-tert-butyl-N$^2$—Z-D-serinamide(VIII)

To a cooled (–20° C.) solution of N—Z—O-tert-butyl-D-serine (2.5 g) in tetrahydrofuran (35 mL), triethylamine (1.3 mL) was added and stirred for 5 minutes and isobutylchloformate (1.67 mL) was added in 5 minutes at –20° C. The solution was stirred for 5 minutes at –20° C. and benzyl amine (1.37 mL) was added to the reaction mixture in 5 minutes at –20° C. The solution was stirred for 45 minutes at –20° C. The solution was allowed to warm at room temperature and stirred for 1 hour. The hydrochloride salt of N-methylmorpholine was filtered. Organic layer was concentrated under vacuum to obtain solid 1.1 g N-benzyl-O-tert-butyl-N$^2$—Z-D-serinamide after crystallization by diisopropylether.
HPLC Purity: 91.33%, Mass 385.11 (M+H), % Yield: 34%.

Example 51

Preparation of N-benzyl-O-tert-butyl-N$^2$—Z-D-serinamide(VIII)

To a cooled (–20° C.) solution of N—Z—O-tert-butyl-D-serine (0.5 g) in tetrahydrofuran (4 mL), N-methylmorpholine (0.27 mL) was added and stirred for 5 minutes and methylchloformate (0.3 mL) was added to it in 5 minutes at –20° C. The solution was stirred for 5 minutes at –20° C. and benzyl amine (0.27 mL) was added to the reaction mixture in 5 minutes at –20° C. The solution was stirred for 45 minutes at –20° C. The solution was allowed to warm to room temperature and stirred for 1 hour. The hydrochloride salt of N-methylmorpholine was filtered. Organic layer was concentrated under vacuum to obtain solid 0.29 g N-benzyl-O-tert-butyl-N$^2$—Z-D-serinamide after crystallization by diisopropylether.
HPLC Purity: 85%, Mass 385.10 (M+H), % Yield: 45%.

Example 52

Preparation of N-benzyl-O-tert-butyl-N$^2$—Z-D-serinamide(VIII)

To a cooled (–20° C.) solution of N—Z—O-tert-butyl-D-serine (25 g) tetrahydrofuran (350 mL), N-methylmorpholine (13.9 mL) was added and stirred for 5 minutes and isobutylchloformate (16.67 mL) was added to the reaction mixture in 5 minutes at –20° C. The solution was stirred for 5 minutes at –20° C. and benzyl amine (13.87 mL) was added to the reaction mixture in 5 minutes at –20° C. The solution was stirred for 45 minutes at –20° C. The solution was allowed to warm at room temperature and stirred for 1 hour. The hydrochloride salt of N-methylmorpholine was filtered. Organic layer was concentrated under vacuum to obtain solid 29.7 g N-benzyl-O-tert-butyl-N$^2$—Z-D-serinamide after crystallization by diisopropylether.
Yield: 29.7 g, HPLC Purity: 99.33%; MS=385.0 [M$^+$+1,100]; Yield=91%; [α]$_D^{25}$ (c=1% in DMF)=–1.69°; $^1$H NMR (DMSO-d$^6$)=δ1.09 (s, CH$_3$—Bu$^t$), δ3.49 (m, NHCH$_2$Ph), δ4.13 (m, CH), δ4.25 (dd, J=5.6 Hz, CHH' OBu$^t$), δ4.35 (dd, J=6.0 Hz, CHH' OBu$^t$), δ5.03 (s, OCH$_2$Ph), δ7.18-7.35 (m PhHCH$_2$NH, PhHCH$_2$O and NHCH) δ8.42 (t, NHCH$_2$Ph); $^{13}$C NMR (DMSO-d$^6$) δ27.1 (C(CH$_3$)$_3$), δ65.4 (CH$_2$O), δ41.9 (NHCH$_2$Ph), δ55.4 (CH), δ72.6 (C(CH$_3$)$_3$), δ126.6-139.2 (Ph), δ169.9 (C(O)NH); IR (KBr) 3333.1, 3308.0, 2974.3, 1685.8, 1651.1, 1533.4, 1469.8, 1365.6, 1294.2, 1230.6, 1037.7, 696.3. cm$^{-1}$

Example 53

Preparation of N-benzyl-O-tert-butyl-D-serinamide(IX)

10% Palladium charcoal (1 g) was charged to a solution N-benzyl-O-tert-butyl-N$^2$—Z-D-serinamide (5 g) in methanol (50 mL). Subsequent stirring and hydrogenation for 2 hrs led to complete conversion. Catalyst was filtered and concentrated to give 3.2 g N-benzyl-O-tert-butyl-D-serinamide.
Yield: 3.2 g, HPLC Purity: 87.15%, Mass 251.26 (M+H), % Yield: 100%.

Example 54

Preparation of N-benzyl-O-tert-butyl-D-serinamide(IX)

10% Palladium charcoal (0.1 g) was charged to a solution N-benzyl-O-tert-butyl-N$^2$—Z-D-serinamide (0.5 g) in ethanol (5 mL). Subsequent stirring and hydrogenation for 2 hrs at room temperature. Catalyst was filtered and concentrated to give 0.22 g N-benzyl-O-tert-butyl-D-serinamide oil.
HPLC Purity: 85%, Mass 251.29 (M+H), % Yield: 67%.

Example 55

Preparation of N-benzyl-O-tert-butyl-D-serinamide(IX)

5% Palladium charcoal (0.2 g) was charged to a solution N-benzyl-O-tert-butyl-N$^2$—Z-D-serinamide (0.5 g) in methanol (5 mL). Subsequent stirring and hydrogenation for 2 hrs at room temperature. Catalyst was filtered and concentrated to give 0.12 g N-benzyl-O-tert-butyl-D-serinamide oil.
HPLC Purity: 81%, Mass 251.00 (M+H), % Yield: 37%.

Example 56

Preparation of N-benzyl-O-tert-butyl-D-serinamide(IX)

10% Palladium charcoal (0.1 g) was charged to a solution N-benzyl-O-tert-butyl-N$^2$—Z-D-serinamide (0.5 g) in methanol (5 mL) along with catalytic amount of acetic acid (0.1 mL). Subsequent stirring and hydrogenation for 2 hrs at room temperature. Catalyst was filtered and concentrated to give 0.28 g N-benzyl-O-tert-butyl-D-serinamide oil.
HPLC Purity: 95%, Mass 251.19 (M+H), % Yield: 86%.

Example 57

Preparation of N-benzyl-O-tert-butyl-D-serinamide(IX)

10% Palladium charcoal (1.1 g) was charged to a solution N-benzyl-O-tert-butyl-N$^2$—Z-D-serinamide (5.5 g) in methanol (110 mL). Subsequent stirring and hydrogenation for 4 hrs at room temperature led to complete conversion. Catalyst was filtered and concentrated to give 3.0 g N-benzyl-O-tert-butyl-D-serinamide oil.
HPLC Purity: 95%, Mass 251.26 (M+H), % Yield: 83%

Example 58

Preparation of N-benzyl-O-tert-butyl-D-serinamide(IX)

10% Palladium charcoal (0.1 g) was charged to a solution N-benzyl-O-tert-butyl-N$^2$—Z-D-serinamide (0.5 g) in methanol (5 mL). Subsequent stirring and hydrogenation for 2 hrs at 40° C. led to complete conversion. Catalyst was filtered and concentrated to give 0.22 g N-benzyl-O-tert-butyl-D-serinamide oil.
HPLC Purity: 89%, Mass 251.26 (M+H), % Yield: 68%.

Example 59

Preparation of N-benzyl-O-tert-butyl-D-serinamide(IX)

10% Palladium charcoal (5.8 g) was charged to a solution N-benzyl-O-tert-butyl-N$^2$—Z-D-serinamide (29 g) in methanol (580 mL). Subsequent stirring and hydrogenation for 2 hrs at room temperature led to complete conversion. Catalyst was filtered and concentrated to give 18.89 g N-benzyl-O-tert-butyl-D-serinamide oil.
Yield: 18.89 g; HPLC Purity: 98.04%; MS=250.8 [M$^+$+1, 100], Yield=100%; [α]$_D^{25}$ (c=1% in DMF)=+4.65°; $^1$H NMR (DMSO-d$^6$)=δ1.12 (s, CH$_3$—Bu$^t$), δ2.56 (br. s, free —NH$_2$), δ3.36 (m, CHNH$_2$), δ3.43 (d, CH$_2$Ph), δ4.33 (m, CH$_2$OtBut), δ7.20-7.30 (m, PhH), δ8.43 (t, NHCH$_2$Ph); $^{13}$C NMR (DMSO-d$^6$) δ27.2 (C(CH$_3$)$_3$), δ41.8 (CH$_2$Ph), δ55.1 (CH), δ64.2 (CH$_2$OBu$^t$), δ72.3 (C(CH$_3$)$_3$), δ126.5 (C$_4$'), δ126.9 (2C$_2$' or 2C$_3$'), δ128.0' (2C$_2$' or 2C$_3$'), δ139.5 (C$_1$'), δ172.7 (C(O)NH); IR (KBr) 3365.9, 3016.7, 2976.2, 2933.8, 1660.7, 1521.8, 1454.3, 1365.6, 1217.1, 1082.1, 771.5. cm$^{-1}$.

Example 60

Preparation of N-benzyl-O-tert-butyl-N$^2$-acetyl-D-serinamide(X)

To a clear solution of N-benzyl-O-tert-butyl-D-serinamide (1 g), 4-dimethylaminopyridine (25 mg) and dichloromethane (5 mL), acetic anhydride was added at room temperature. The solution was stirred for 1.5 hours at room temperature. The dichloromethane layer was sequentially washed by water (15 mL), 5% NaHCO$_3$ solution (15 mL), water (15 mL) and brine solution 15 mL to make neutral pH. Organic layer was concentrated under vacuum to obtain solid 0.8 g N-benzyl-O-tert-butyl-N$^2$-acetyl-D-serinamide after crystallization by diisopropylether.
Yield: 0.8 g, HPLC Purity: 98.11%, Mass 293.26 (M+H), % Yield: 69%

Example 61

Preparation of N-benzyl-O-tert-butyl-N$^2$-acetyl-D-serinamide(X)

To a clear solution of N-benzyl-O-tert-butyl-D-serinamide (0.1 g), 4-dimethylaminopyridine (0.25 mg) and ethyl acetate (0.5 mL), acetic anhydride (0.045 mL) was added at room temperature. The solution was stirred for 1.5 hours at room temperature. The dichloromethane layer was sequentially washed by water, 5% NaHCO₃ solution, water and brine solution to make neutral pH. Organic layer was concentrated under vacuum to obtain solid 0.05 g N-benzyl-O-tert-butyl-N²-acetyl-D-serinamide after crystallization by diisopropylether.
HPLC Purity: 91.21%, Mass 293.62 (M+H), % Yield: 43%.

Example 62

Preparation of N-benzyl-O-tert-butyl-N²-acetyl-D-serinamide(X)

To a clear solution of N-benzyl-O-tert-butyl-D-serinamide (0.2 g), 4-dimethylaminopyridine (0.5 mg) and pyridine (1 mL), acetic anhydride (0.09 mL) were added at room temperature. The solution was stirred for 1.5 hours at room temperature. The dichloromethane layer was sequentially washed by water, 5% NaHCO₃ solution, water and brine solution to make neutral pH. Organic layer was concentrated under vacuum to obtain solid 0.07 g N-benzyl-O-tert-butyl-N²-acetyl-D-serinamide after crystallization by diisopropylether.
HPLC Purity: 89.11%, Mass 293.19 (M+H), % Yield: 30%.

Example 63

Preparation of N-benzyl-O-tert-butyl-N²-acetyl-D-serinamide(X)

To a clear solution of N-benzyl-O-tert-butyl-D-serinamide (0.1 g), pyridine (0.25 mg) and dichloromethane (0.5 mL), acetic anhydride (0.045 mL) was added at room temperature. The solution was stirred for 1.5 hours at room temperature. The dichloromethane layer was sequentially washed by water, 5% NaHCO₃ solution, water and brine solution to make neutral pH. Organic layer was concentrated under vacuum to obtain solid 0.03 g N-benzyl-O-tert-butyl-N²-acetyl-D-serinamide after crystallization by diisopropylether.
HPLC Purity: 85.2%, Mass 293.11 (M+H), % Yield: 26%.

Example 64

Preparation of N-benzyl-O-tert-butyl-N²-acetyl-D-serinamide(X)

To a clear solution of N-benzyl-O-tert-butyl-D-serinamide (18 g), 4-dimethylaminopyridine (0.44 g) and dichloromethane (90 mL), acetic anhydride (8.1 mL) was added at room temperature. The solution was stirred for 1.5 hours at room temperature. The dichloromethane layer was sequentially washed by water, 5% NaHCO₃ solution, water and brine solution to make neutral pH. Organic layer was concentrated under vacuum to obtain solid 17.8 g N-benzyl-O-tert-butyl-N²-acetyl-D-serinamide after crystallization by diisopropylether.
Yield: 17.8 g, HPLC Purity: 99.9%; MS=292.9 [M⁺+1, 100], Yield=85%; [α]$_D^{25}$ (c=1% in DMF)=+2.30°; M.P=136.8° C.; 1H NMR=δ1.10 (s, CH₃-tBut), δ1.85 (s, C(O)CH₃), δ¹H NMR (DMSO-d⁶) δ1.10 (CH₃Buʳ), δ1.85 (s, C(O)CH₃), δ3.46 (dd, CH₂OtBut), δ4.24 (m, CH), δ4.35 (d, CH₂Ph), δ7.19-7.30 (m, PhH), δ7.89 (d, C(O)NH), δ8.41 (t, NHCH₂Ph); ¹³C NMR (DMSO-d⁶) δ22.5 (C(O)CH₃), δ27.1 (C(CH₃)₃), δ41.8 (CH₂Ph), δ53.3 (CH), δ61.9 (CH₂OBuʳ), δ72.7 (C(CH₃)₃), δ126.5 (C₄'), δ126.8 (2C₂' or 2C₃'), δ128.0' (2C₂' or 2C₃'), δ139.3 (C₁'), δ169.2 (C(O)CH₃ or C(O)NH), δ170.0 (C(O)CH₃ or C(O)NH); IR (KBr) 3281.0, 3064.9, 2978.1, 1635.6, 1541.1, 1367.5, 1087.8, 750.3 cm⁻¹.

Example 65

Preparation of N-benzyl-N²-acetyl-D-serinamide(VI)

To a solution of N-benzyl-O-tert-butyl-N²-acetyl-D-serinamide (0.7 g) and dichloromethane (15 mL), trifluoroacetic acid (7 mL) was added. The solution was stirred for 2 hours for completion of reaction and after workup and crystallization gave solid 0.55 g N-benzyl-N²-acetyl-D-serinamide.
Yield: 0.55 g, HPLC Purity: 82.49%, Mass 237.25 (M+H), % Yield: 98%

Example 66

Preparation of N-benzyl-N²-acetyl-D-serinamide

To a solution of N-benzyl-O-tert-butyl-N²-acetyl-D-serinamide (0.5 g) and dichloromethane (10 mL), aq. HCl 35% (5 mL) was added. The solution was stirred for 2 hours at room temperature for completion of reaction and after workup and crystallization gave solid 0.21 g N-benzyl-N²-acetyl-D-serinamide.
HPLC Purity: 81.9%, Mass 237.21 (M+H), % Yield: 52%

Example 67

Preparation of N-benzyl-N²-acetyl-D-serinamide(VI)

To a solution of N-benzyl-O-tert-butyl-N²-acetyl-D-serinamide (0.5 g) and dichloromethane (10 mL), aq. HCl 20% (5 mL) was added. The solution was stirred for 4 hours at room temperature for completion of reaction and after workup and crystallization gave solid 0.1 g N-benzyl-N²-acetyl-D-serinamide.
HPLC Purity: 78.9%, Mass 237.11 (M+H), % Yield: 25%.

Example 68

Preparation of N-benzyl-N²-acetyl-D-serinamide(VI)

To a solution of N-benzyl-O-tert-butyl-N²-acetyl-D-serinamide (0.5 g) and dichloromethane (10 mL), aq. HCl 30% (5 mL) was added. The solution was stirred for 3.5 hours at room temperature for completion of reaction and after workup and crystallization gave solid 0.12 g N-benzyl-N²-acetyl-D-serinamide.
HPLC Purity: 76.1%, Mass 237.23 (M+H), % Yield: 30%.

Example 69

Preparation of N-benzyl-N²-acetyl-D-serinamide(VI)

To a solution of N-benzyl-O-tert-butyl-N²-acetyl-D-serinamide (0.7 g) and dichloromethane (15 mL), trifluoroacetic acid (7 mL) was added. The solution was stirred for 1.5 hours at 40° C. for completion of reaction and after workup and crystallization gave solid 0.4 g N-benzyl-N²-acetyl-D-serinamide.
HPLC Purity: 83.33%, Mass 237.21 (M+H), % Yield: 70%.

Example 70

Preparation of N-benzyl-N²-acetyl-D-serinamide(VI)

To a solution of N-benzyl-O-tert-butyl-N²-acetyl-D-serinamide (17 g) and dichloromethane (170 mL), trifluoroacetic acid (170 mL) was added. The solution was stirred for 2 hours at room temperature for completion of reaction and after workup and crystallization gave solid 11.6 g N-benzyl-N²-acetyl-D-serinamide.
Yield: 11.6 g, HPLC Purity: 99.14%, Mass 258.8 (M+Na), % Yield: 85%; mp=137.3° C.; $[\alpha]_D^{25}$ (c=1% in DMF)=+5.75°; $^1$H NMR (DMSO-d$^6$) δ1.86 (s, C(O)CH$_3$), δ3.58 (d, CH$_2$), δ4.27-4.31 (m, CH and NHCH$_2$), δ4.89 (s, OH), δ7.18-7.30 (m, PhH), δ7.91 (d, C(O)NH), δ8.35 (t, NHCH$_2$Ph); $^{13}$C NMR (DMSO-d$^6$) δ22.6 (C(O)CH$_3$), δ41.9 (NHCH$_2$Ph), δ55.3 (CH), δ61.7 (CH$_2$O), δ126.5 (C$_4$'), δ126.9 (2C$_2$' or 2C$_3$'), δ128.1' (2C$_2$' or 2C$_3$'), δ139.3 (C$_1$'), δ169.4 (C(O)CH$_3$ or C(O)NH), δ170.1 (C(O)CH$_3$ or C(O)NH); IR (KBr) 3325.3, 3192.3, 2960.8, 1635.6, 1558.5, 1379.1, 1053.1731.0 cm$^{-1}$.

Example-71

Preparation of N-benzyl-O-methyl-N²-acetyl-D-serinamide, Lacosamide

To a solution of dichloromethane (40 mL) and N-benzyl-N²-acetyl-D-serinamide (4 g) tetrabutylammonium bromide (545 mg) was added followed by 20% NaOH (3.38 mL) at room temperature. Subsequently, dimethylsulphate (6.58 mL) and 50% NaOH (6.08 mL) were added. The solution was stirred for 3 hours at room temperature. Organic layer was separated and washed by water (80 mL). Organic layer was concentrated under vacuum to obtain solid 2.75 g Lacosamide after crystallization by diisopropylether.
Yield: 2.75 g, HPLC Purity: 76.821%, % Yield: 65%.

Example-72

Preparation of N-benzyl-O-methyl-N²-acetyl-D-serinamide, Lacosamide

To a solution of toluene (22 mL) and N-benzyl-N²-acetyl-D-serinamide (1.1 g) tetrabutylammonium bromide (0.075 g) was added followed by 20% NaOH (1.02 mL) at room temperature. Subsequently, dimethylsulphate (1.8 mL) and 50% NaOH (1.6 mL) were added. The solution was stirred for 3 hours at room temperature. Organic layer was separated and washed by water. Organic layer was concentrated under vacuum to obtain solid 0.7 g Lacosamide after crystallization by diisopropylether.
Crude compound (0.7 g) was stirred with mixture of Toluene: Ethyl acetate 1:1 (19.5 mL) for one hour at for one hour at room temperature, filter to get white solid compound 0.34 g. HPLC Purity: 96.1%, Mass 250.8 (M+H), % Yield: 29%.

Example-73

Preparation of N-benzyl-O-methyl-N²-acetyl-D-serinamide, Lacosamide

To a solution of dichloromethane (20 mL) and N-benzyl-N²-acetyl-D-serinamide (1 g) tetrabutylammonium bromide (0.069 g) was added followed by 20% NaOH (0.93 mL) at room temperature. Subsequently, dimethylsulphate (1.92 mL, 5 m.eq.) and 50% NaOH (1.52 mL) were added. The solution was stirred for 3 hours at room temperature. Organic layer was separated and washed by water (20 mL). Organic layer was concentrated under vacuum to obtain solid 0.6 g Lacosamide after crystallization by diisopropylether.
Crude compound (0.6 g) was stirred with mixture of Toluene: Ethyl acetate 1:1 (15 mL) for one hour at for one hour at room temperature, filter to get white solid compound 0.30 g. % Yield: 28%, HPLC Purity: 98%, Mass 251.0 (M+H).

Example-74

Preparation of N-benzyl-O-methyl-N²-acetyl-D-serinamide, Lacosamide

To a solution of dichloromethane (20 mL) and N-benzyl-N²-acetyl-D-serinamide (1 g) tetrabutylammonium bromide (0.069 g) was added followed by 20% NaOH (0.93 mL) at room temperature. Subsequently, dimethylsulphate (0.41 mL, 1 m.eq.) and 50% NaOH (1.52 mL) was added. The solution was stirred for 3 hours at room temperature. Organic layer was separated and washed by water (20 mL). Organic layer was concentrated under vacuum to obtain solid 0.5 g Lacosamide after crystallization by diisopropylether.
Crude compound (0.5 g) was stirred with mixture of Toluene: Ethyl acetate 1:1 (12.5 mL) for one hour at for one hour at room temperature, filter to get white solid compound 0.16 g. % Yield: 15%, HPLC Purity: 78.8%.

Example-75

Preparation of N-benzyl-O-methyl-N²-acetyl-D-serinamide, Lacosamide

To a solution of dichloromethane (20 mL) and N-benzyl-N²-acetyl-D-serinamide (1 g) tetrabutylammonium bromide (0.013 g, 0.01 m.eq.) was added followed by 20% NaOH (0.93 mL) at room temperature. Subsequently, dimethylsulphate (1.64 mL) and 50% NaOH (1.52 mL) was added. The solution was stirred for 13 hours at room temperature. Organic layer was separated and washed by water (20 mL). Organic layer was concentrated under vacuum to obtain solid 0.40 g Lacosamide after crystallization by diisopropylether.
Crude compound (0.40 g) was stirred with mixture of Toluene:Ethyl acetate 1:1 (10 mL) for one hour at for one hour at room temperature, filter to get white solid compound 0.11 g., % Yield: 10%, HPLC Purity: 85%.

Example-76

Preparation of N-benzyl-O-methyl-N²-acetyl-D-serinamide, Lacosamide

To a solution of dichloromethane (20 mL) and N-benzyl-N²-acetyl-D-serinamide (1 g) tetrabutylammonium bromide (0.136 g, 0.1 m.eq.) was added followed by 20% NaOH (0.93 mL) at room temperature. Subsequently, dimethylsulphate (1.64 mL) and 50% NaOH (1.52 mL) was added. The solution was stirred for 3 hours at room temperature. Organic layer was separated and washed by water (20 mL). Organic layer was concentrated under vacuum to obtain solid 0.7 g Lacosamide after crystallization by diisopropylether.
Crude compound (0.7 g) was stirred with mixture of Toluene: Ethyl acetate 1:1 (17.5 mL) for one hour at for one hour at room temperature, filter to get white solid compound 0.26 g., % Yield: 24%, HPLC Purity: 91%

Example-77

Preparation of N-benzyl-O-methyl-N²-acetyl-D-serinamide, Lacosamide

To a solution of dichloromethane (3 mL, 3 vol.) and N-benzyl-N²-acetyl-D-serinamide (1 g) tetrabutylammonium bromide (0.069 g) was added followed by 20% NaOH (0.93 mL) at room temperature. Subsequently, dimethylsulphate (1.64 mL) and 50% NaOH (1.52 mL) was added. The solution was stirred for 3 hours at room temperature. Organic layer was separated and washed by water (20 mL). Organic layer was concentrated under vacuum to obtain solid 0.35 g Lacosamide after crystallization by diisopropylether.

Crude compound (0.35 g) was stirred with mixture of Toluene:Ethyl acetate 1:1 (8.75 mL) for one hour at for one hour at room temperature, filter to get white solid compound 0.13 g. % Yield: 12%, HPLC Purity: 79%.

Example-78

Preparation of N-benzyl-O-methyl-$N^2$-acetyl-D-serinamide, Lacosamide

To a solution of dichloromethane (10 mL, 10 vol) and N-benzyl-$N^2$-acetyl-D-serinamide (1 g) tetrabutylammonium bromide (0.069 g) was added followed by 20% NaOH (0.93 mL) at room temperature. Subsequently, dimethylsulphate (1.64 mL) and 50% NaOH (1.52 mL) was added. The solution was stirred for 4 hours at room temperature. Organic layer was separated and washed by water (20 mL). Organic layer was concentrated under vacuum to obtain solid 0.51 g Lacosamide after crystallization by diisopropylether.

Crude compound (0.51 g) was stirred with mixture of Toluene:Ethyl acetate 1:1 (12.7 mL) for one hour at for one hour at room temperature, filter to get white solid compound 0.26 g., % Yield: 25%, HPLC Purity: 93%.

Example-79

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (4.23 mL, 5 m.eq.) at room temperature. Subsequently, dimethylsulphate (1.64 mL) and 50% NaOH (1.52 mL) was added. The solution was stirred for 3 hours at room temperature. Organic layer was separated and washed by water (20 mL). Organic layer was concentrated under vacuum to obtain solid 0.44 g Lacosamide after crystallization by diisopropylether.

Crude compound (0.44 g) stir with mixture of Toluene:Ethyl acetate 1:1 (11 mL) for one hour at for one hour at room temperature, filter to get white solid compound 0.16 g., % Yield: 15%, HPLC Purity: 90.1%.

Example-80

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (8.56 mL, 10 m.eq.) at room temperature. Subsequently, dimethylsulphate (1.64 mL) and 50% NaOH (1.52 mL) was added. The solution was stirred for 3 hours at room temperature. Organic layer was separated and washed by water (20 mL). Organic layer was concentrated under vacuum to obtain solid 0.31 g Lacosamide after crystallization by diisopropylether.

Crude compound (0.31 g) was stirred with mixture of Toluene:Ethyl acetate 1:1 (7.7 mL) for one hour at for one hour at room temperature, filter to get white solid compound 0.11 g., % Yield: 10%, HPLC Purity: 85%.

Example-81

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 5% NaOH (3.72 mL, 1.1 m.eq.) at room temperature. Subsequently, dimethylsulphate (1.64 mL) and 50% NaOH (1.52 mL) was added. The solution was stirred for 10 hours at room temperature. Organic layer was separated and washed by water (20 mL). Organic layer was concentrated under vacuum to obtain solid 0.51 g Lacosamide after crystallization by diisopropylether.

Crude compound (0.51 g) was stirred with mixture of Toluene:Ethyl acetate 1:1 (12.5 mL) for one hour at for one hour at room temperature, filter to get white solid compound 0.22 g., % Yield: 21%, HPLC Purity: 95%

Example-82

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 10% NaOH (1.86 mL, 1.1 m.eq.) at room temperature. Subsequently, dimethylsulphate (1.64 mL) and 50% NaOH (1.52 mL) was added. The solution was stirred for 10 hours at room temperature. Organic layer was separated and washed by water (20 mL). Organic layer was concentrated under vacuum to obtain solid 0.60 g Lacosamide after crystallization by diisopropylether.

Crude compound (0.60 g) was stirred with mixture of Toluene:Ethyl acetate 1:1 (15 mL) for one hour at for one hour at room temperature, filter to get white solid compound 0.3 g., % Yield: 28%, HPLC Purity: 96.5%

Example-83

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 30% NaOH (0.62 mL, 1.1 m.eq.) at room temperature. Subsequently, dimethylsulphate (1.64 mL) and 50% NaOH (1.52 mL) was added. The solution was stirred for 10 hours at room temperature. Organic layer was separated and washed by water (20 mL). Organic layer was concentrated under vacuum to obtain solid 0.64 g Lacosamide after crystallization by diisopropylether.

Crude compound (0.64 g) stir with mixture of Toluene:Ethyl acetate 1:1 (15 mL) for one hour at for one hour at room temperature, filter to get white solid compound 0.32 g., % Yield: 30%, HPLC Purity: 97.1%

Example-84

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 50% NaOH (0.37 mL, 1.1 m.eq.) at room temperature. Dimethylsulphate (1.64 mL) and 50% NaOH (1.52 mL) were added. The solution was stirred for 10 hours at room temperature. Organic layer was separated and washed by water (20 mL). Organic layer was concentrated under vacuum to obtain solid 0.34 g Lacosamide after crystallization by diisopropylether.

Crude compound (0.34 g) was stirred with mixture of Toluene:Ethyl acetate 1:1 (15 mL) for one hour at for one hour at room temperature, filter to get white solid compound 0.15 g. % Yield: 14%, HPLC Purity: 87.2%

Example-85

Preparation of N-benzyl-O-methyl-$N^2$-acetyl-D-serinamide. Lacosamide

To a solution of dichloromethane (20 mL) and N-benzyl-$N^2$-acetyl-D-serinamide (1 g) tetrabutylammonium bromide (0.069 g) was added followed by 20% NaOH (0.93 mL) at room temperature. Subsequently, dimethylsulphate (1.64 mL) and 50% NaOH (3.38 mL, 10 m.eq.) was added. The solution was stirred for 3 hours at room temperature. Organic layer was separated and washed by water (20 mL). Organic layer was concentrated under vacuum to obtain solid 0.61 g Lacosamide after crystallization by diisopropylether.

Crude compound (0.61 g) was stirred with mixture of Toluene:Ethyl acetate 1:1 (15.25 mL) for one hour at for one hour at room temperature, filter to get white solid compound 0.3 g. % Yield: 28%, HPLC Purity: 56%

Example-86

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (0.93 mL) at room temperature. Subsequently, dimethylsulphate (1.64 mL) and 50% NaOH (0.33 mL, 1 m.eq.) was added. The solution was stirred for 3 hours at room temperature. Organic layer was separated and washed by water (20 mL). Organic layer was concentrated under vacuum to obtain solid 0.65 g Lacosamide after crystallization by diisopropylether.

Crude compound (0.65 g) was stirred with mixture of Toluene:Ethyl acetate 1:1 (16.25 mL) for one hour at for one hour at room temperature, filter to get white solid compound 0.28 g. % Yield: 26%, HPLC Purity: 46%

Example-87

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (0.93 mL) at room temperature. Subsequently, dimethylsulphate (1.64 mL) and 5% NaOH (30.4 mL) was added. The solution was stirred for 3 hours at room temperature. Organic layer was separated and washed by water (20 mL). Organic layer was concentrated under vacuum to obtain solid 0.49 g Lacosamide after crystallization by diisopropylether.

Crude compound (0.49 g) was stirred with mixture of Toluene:Ethyl acetate 1:1 (12.25 mL) for one hour at for one hour at room temperature, filter to get white solid compound 0.26 g, % Yield: 25%, HPLC Purity: 91%

Example-88

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (0.93 mL) at room temperature. Subsequently, dimethylsulphate (1.64 mL) and 10% NaOH (15.2 mL) was added. The solution was stirred for 3 hours at room temperature. Organic layer was separated and washed by water (20 mL). Organic layer was concentrated under vacuum to obtain solid 0.51 g Lacosamide after crystallization by diisopropylether.

Crude compound (0.51 g) stir with mixture of Toluene:Ethyl acetate 1:1 (12.75 mL) for one hour at for one hour at room temperature, filter to get white solid compound 0.29 g., % Yield: 27%, HPLC Purity: 93%

Example-89

Preparation of N-benzyl-O-methyl-$N^2$-acetyl-D-serinamide, Lacosamide

To a solution of dichloromethane (20 mL) and N-benzyl-$N^2$-acetyl-D-serinamide (1 g) tetrabutylammonium bromide (0.069 g) was added followed by 20% NaOH (0.93 mL) at room temperature. Subsequently, dimethylsulphate (1.64 mL) and 30% NaOH (5.06 mL) was added. The solution was stirred for 3 hours at room temperature. Organic layer was separated and washed by water (20 mL). Organic layer was concentrated under vacuum to obtain solid 0.59 g Lacosamide after crystallization by diisopropylether.

Crude compound (0.59 g) stir with mixture of Toluene:Ethyl acetate 1:1 (14.75 mL) for one hour at for one hour at room temperature, filter to get white solid compound 0.31 g., % Yield: 29%, HPLC Purity: 96%

Example-90

Preparation of N-benzyl-O-methyl-$N^2$-acetyl-D-serinamide, Lacosamide

To a solution of dimethyl sulfoxide (2.5 mL) and N-benzyl-$N^2$-acetyl-D-serinamide (0.1 g) was added followed by 50% KOH (1.25 mL) at room temperature. Subsequently, dimethylsulphate (0.02 mL) and 10% KOH (0.12 mL) was added. The solution was stirred for 16 hours at room temperature. Reaction mixture was dumped in to the water and product extracted by dichloromethane. Organic layer was separated and washed by water (2 mL). Organic layer was concentrated under vacuum to obtain solid 0.06 g Lacosamide after crystallization by diisopropylether.

Crude compound (0.065 g) was stirred with mixture of Toluene:Ethyl acetate 1:1 (1.62 mL) for one hour at for one hour at room temperature, filter to get white solid compound 0.026 g, % Yield: 25%, HPLC Purity: 79%

Example 91

Preparation of N-benzyl-O-methyl-$N^2$-acetyl-D-serinamide, Lacosamide

To a solution of acetonitrile (2 mL) and N-benzyl-$N^2$-acetyl-D-serinamide (0.1 g) methyl iodide (0.069 g) was added at 0 to 5° C. silver dioxide (0.2 g) was added. The solution was stirred for 19 hours at room temperature. Solid was filtered and filtrate was distilled out, and then dump in to water and compound was extracted by dichloromethane. Organic layer was separated and washed by water. Organic layer was concentrated under vacuum to obtain solid 0.05 g Lacosamide after crystallization by Diisopropylether purified by toluene:ethyl acetate (1:1).

Yield 0.021 g, % Yield: 20%, HPLC Purity: 81%

Example 92

Preparation of N-benzyl-O-methyl-$N^2$-acetyl-D-serinamide, Lacosamide

To a solution of tetrahydrofuran (2 mL) and N-benzyl-$N^2$-acetyl-D-serinamide (0.1 g) added followed methyl iodide (0.3 mL) at 0 to 5° C. Sodium hydride was added (0.05 g)) was added at same temperature. The solution was stirred for 3 hours at room temperature. Reaction mixture was dumped in to the water and product was extracted by dichloromethane. Organic layer was separated and washed by water (2 mL). Organic layer was concentrated under vacuum to obtain solid 0.05 g Lacosamide after crystallization by diisopropylether.

Crude compound (0.05 g) was stirred with mixture of Toluene:Ethyl acetate 1:1 (1.25 mL) for one hour at for one hour at room temperature, filter to get white solid compound 0.02 g, % Yield: 19%, HPLC Purity: 79%

Example 93

Preparation of N-benzyl-O-methyl-$N^2$-acetyl-D-serinamide, Lacosamide

To a solution of dichloromethane (220 mL) and N-benzyl-$N^2$-acetyl-D-serinamide (11 g) tetrabutylammonium bromide (0.75 g) was added followed by 20% NaOH (10.24 mL) at room temperature. Dimethylsulphate (18.06 mL) and 50% NaOH (16.75 mL) were added. The solution was stirred for 3 hours at room temperature. Organic layer was separated and washed by water (220 mL). Organic layer was concentrated under vacuum to obtain solid 7.8 g Lacosamide after crystallization by diisopropylether.

Yield: 7.8 g, HPLC Purity: 96.65%

Crude compound 7.8 g was stirred with mixture of Toluene:Ethyl acetate 1:1 (195 mL) for one hour at for one hour at room temperature, filter to get white solid compound 4 g.

Yield 4 g, % Yield: 34%,

HPLC Purity: 99.68%; Chiral Purity: 99.06%; Specific Optical Rotation (c=1, MeOH)=+15.08°; mp=144.0° C.;

IR (KBr) 3291, 3086, 2924, 2876, 2807, 1638, 1547, 1138, 694 $cm^{-1}$;

$^1$H NMR (DMSO) δ1.86 (s, $C(O)CH_3$), δ3.24 (s, $OCH_3$), δ3.49 (m, $CH_2OCH_3$), δ4.28 (d, J=6.0 Hz, $NHCH_2$), δ4.45-4.50 (m, CH), δ8.08 (d, J=8.0 Hz, NH), δ8.46 (t, J=5.8 Hz, NH), δ7.19-7.31 (m, PhH).

$^{13}$C NMR (DMSO), δ22.54 ($C(O)CH_3$), δ41.99 ($CH_2NH$), δ52.64 (CH), δ58.16 ($OCH_3$), δ72.11 ($CH_2OCH_3$), δ126.6 ($C_4'$), δ126.9 ($2C_2'$ or $2C_3'$), δ128.1 ($2C_2'$ or $2C_3'$), δ139.2 ($C_1'$), δ169.3 ($C(O)CH_3$ or C(O)NH), δ169.7 ($C(O)CH_3$ or C(O)NH) ppm; MS 250.9 [$M^+$+1, 100]; Anal. ($C_{13}H_{18}N_2O_3$) C, H, N.

Example-94

Process for the Purification of Lacosamide

Crude Lacosamide 0.5 g was stirred with MTBE (10 mL) at room temperature for 2 hours, filter to get white solid compound 0.42 g. Purity 99.10%

Example-95

Process for the Purification of Lacosamide

Crude Lacosamide 0.5 g was dissolved in Acetone (5 mL), clear solution was observed after heating. Recrystallized the compound by adding DIPE (35 mL) at room temperature, filter to get white solid compound 0.36 g. Purity 99.38%.

Example-96

Process for the Purification of Lacosamide

Crude Lacosamide 0.5 g was dissolved in Acetonitrile (4 mL), clear solution was observed after heating. Recrystallized the compound by adding DIPE (35 mL) at room temperature, filter to get white solid compound 0.350 g. Purity 99.29%

Example-97

Process for the Purification of Lacosamide

Crude Lacosamide 0.5 g was dissolved in DCM (2 mL), clear solution was observed after heating. Recrystallized the compound by adding DIPE (50 mL) at room temperature, filter to get white solid compound 0.405 g. Purity 98.95%

Example-98

Process for the Purification of Lacosamide

Crude Lacosamide 0.5 g was dissolved in IPA (3 mL), clear solution was observed after heating. Recrystallized the compound by adding DIPE (50 mL) at room temperature, filter to get white solid compound 0.3 g. Purity 99.53%

Example-99

Process for the Purification of Lacosamide

Crude Lacosamide 0.5 g was stir with mixture of Ethyl acetate:Toluene (1:1) (15 mL) at room temperature 30 min., filter to get white solid compound 0.38 g. Purity 99.33%

Example-100

Process for the Purification of Lacosamide

Crude Lacosamide 1.0 g was refluxed overnight in Toluene (20 mL), clear solution was observed. Next day stirred it for 30 min. at room temperature, filter to get white solid compound 0.86 g. Purity 99.72%

Example-101

Process for the Purification of Lacosamide

Lacosamide 1.0 g was dissolved in MeOH (2.5 mL), stirred it for 30 min. at room temperature, added DIPE (120 mL).

Solid was observed, filter and washed it with DIPE to get white solid compound 0.78 g. Purity 99.31%

Example-102

Process for the Purification of Lacosamide

Lacosamide 1.0 g was stirred in THF (10 mL) for 30 min. at room temperature and warmed to get dissolved at 40° C. Added n-hexane (150 mL) dropwise. Solid was observed, filter and washed it with n-hexane to get white solid compound 0.83 g. Purity 99.12%

Example-103

Process for the Purification of Lacosamide

Lacosamide 0.5 g was added in acetone (3 mL) at room temperature and warmed to get dissolved at 40° C. Added DIPE (40 mL) and stirred it for 30 min. White solid was observed, filter and washed it with DIPE to get white solid compound 0.40 g. Purity 99.67%

Example-104

Process for the Purification of Lacosamide

Lacosamide 0.5 g was added in IPA (3 mL) at room temperature and warmed to get dissolved at 40° C. Added DIPE (40 mL) and stirred it for 30 min. White solid was observed, filter and washed it with DIPE to get white solid compound 0.35 g. Purity 99.43%

Example-105

Process for the Purification of Lacosamide

Lacosamide 12.0 g was added in IPA (72 mL), and heated at 50° C. to get dissolved. Poured the solution in to the DIPE (1.08 L) at room temperature and stirred it room temperature for 1 hr. Filter it to get white solid compound 9.0 g. Purity 99.69%

While the invention has been described in terms of its specific embodiments, certain modifications and equivalents will be apparent to those skilled in the art and are intended to be included within the scope of the invention.

The invention claimed is:

1. A process for the preparation of lacosamide compound of Formula I,

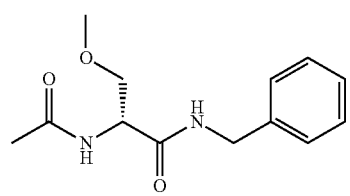

(I)

the process comprising O-methylating the alcoholic group of N-benzyl-$N^2$-acetyl-D-serinamide compound of Formula VI

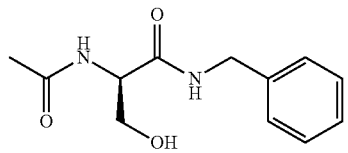

(VI)

with a methylating agent at a temperature between −19° C. and +25° C. in the presence of a base, optionally in the presence of phase transfer catalyst, wherein the methylating agent is selected from the group consisting of dimethyl sulfate and trimethyl phosphate.

2. The process according to claim 1, further comprising adding the methylating agent to a mixture of two phases, wherein the first phase is an aqueous phase comprising a base selected from one or more of sodium hydroxide, lithium hydroxide and potassium hydroxide and the second phase is an organic phase comprising one or more solvents selected from toluene, hexane, methylene dicholoride and methyl tert-butyl ether.

3. The process according to claim 1, wherein the phase transfer catalyst is selected from the group consisting of tetraethyl ammonium p-toluenesulfonate, tetrapropylammonium trifluoromethanesulfonate, tetraphenylphosphonium hexafluoroantimonate, ethylpyridinium bromide, triphenylmethyl triphenyl phosphonium chloride, benzyltriethylammonium chloride, benzyltrimethyl ammonium chloride, benzyltributylammonium chloride, benzyl triphenyl phosphonium chloride, butyltriethyl ammonium bromide, butyltriphenyl phosphonium bromide, cetyltrimethyl ammonium bromide, cetyltrimethyl ammonium chloride, ethyl triphenyl phosphonium bromide, ethyltriphenyl phosphonium iodide, methyltrioctyl ammonium bromide, methyltriphenyl phosphonium bromide, methyltriphenyl phosphonium iodide, phenyltrimethyl ammonium chloride, tetrabutylammonium hydroxide, tetrabutylammonium perchlorate, tetrabutylammonium bromide, tetrabutylammonium hydrogensulphate, tetrabutylammonium iodide, tetrabutylammonium tetrafluoroborate, tetrabutylammonium, thiocyanate, tetraethyl ammonium hydroxide, tetraethyl ammonium iodide, tetramethylammonium chloride, tetraoctyl ammonium bromide, tetraphenylphosphonium bromide, tetrapropyl ammonium hydroxide, tetrapropylammonium bromide and tributylmethyl ammonium chloride.

4. A process for the preparation of lacosamide compound of Formula I,

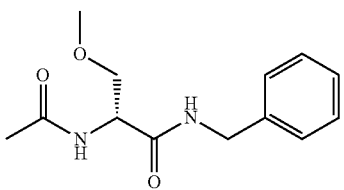

(I)

the process comprising O-methylating the alcoholic group of N-benzyl-$N^2$-acetyl-D-serinamide compound of Formula VI

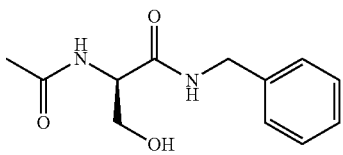

Formula VI with dimethyl sulfate at a temperature between 0° C. to 5° C., wherein the dimethyl sulfate is added to a mixture of two phases optionally in the presence of a phase transfer catalyst, wherein the first phase is an aqueous phase comprising a solution of one or more of aqueous sodium hydroxide and aqueous lithium hydroxide and aqueous potassium hydroxide and the second phase is an organic phase comprising one or more solvents selected from toluene, hexane, methylene dichloride and methyl tert-butyl ether.

5. The process according to claim 4, wherein the phase transfer catalyst is selected from the group consisting of tetraethyl ammonium p-toluenesulfonate, tetrapropylammonium trifluoromethanesulfonate, tetraphenylphosphonium hexafluoroantimonate, ethylpyridinium bromide, triphenylmethyl triphenyl phosphonium chloride, benzyltriethylammonium chloride, benzyltrimethyl ammonium chloride, benzyltributylammonium chloride, benzyl triphenyl phosphonium chloride, butyltriethyl ammonium bromide, butyltriphenyl phosphonium bromide, cetyltrimethyl ammonium bromide, cetyltrimethyl ammonium chloride, ethyl triphenyl phosphonium bromide, ethyltriphenyl phosphonium iodide, methyltrioctyl ammonium bromide, methyltriphenyl phosphonium bromide, methyltriphenyl phosphonium iodide, phenyltrimethyl ammonium chloride, tetrabutylammonium hydroxide, tetrabutylammonium perchlorate, tetrabutylammonium bromide, tetrabutylammonium hydrogensulphate, tetrabutylammonium iodide, tetrabutylammonium tetrafluoroborate, tetrabutylammonium, thiocyanate, tetraethyl ammonium hydroxide, tetraethyl ammonium iodide, tetramethylammonium chloride, tetraoctyl ammonium bromide, tetraphenylphosphonium bromide, tetrapropyl ammonium hydroxide, tetrapropylammonium bromide and tributylmethyl ammonium chloride.

* * * * *